US009365599B2

(12) United States Patent
Hong et al.

(10) Patent No.: US 9,365,599 B2
(45) Date of Patent: Jun. 14, 2016

(54) $N_3S_1$ CHELATOR-FOLATE DERIVATIVES, PREPARATION METHOD THEREOF AND COMPOSITION FOR DIAGNOSIS OR TREATMENT OF CANCER CONTAINING THE SAME AS AN ACTIVE INGREDIENT

(71) Applicant: KOREA ATOMIC ENERGY RESEARCH INSTITUTE, Daejeon (KR)

(72) Inventors: Young-Don Hong, Daejeon (KR); Sun Ju Choi, Daejeon (KR); So-Young Lee, Daejeon (KR); jae cheong Lim, Sejong (KR); Dong Eun Lee, Daejeon (KR)

(73) Assignee: KOREA ATOMIC ENERGY RESEARCH INSTITUTE, Daejeon (KR)

(*) Notice: Subject to any disclaimer, the term of this patent is extended or adjusted under 35 U.S.C. 154(b) by 285 days.

(21) Appl. No.: 14/063,724

(22) Filed: Oct. 25, 2013

(65) Prior Publication Data
US 2014/0121361 A1  May 1, 2014

(30) Foreign Application Priority Data

Oct. 26, 2012  (KR) .................. 10-2012-0119743
Oct. 25, 2013  (KR) .................. 10-2013-0127479

(51) Int. Cl.
*A61K 47/48* (2006.01)
*C07F 13/00* (2006.01)
*C07D 475/04* (2006.01)

(52) U.S. Cl.
CPC ........... *C07F 13/00* (2013.01); *A61K 47/48076* (2013.01); *C07D 475/04* (2013.01)

(58) Field of Classification Search
CPC ................................ A47K 47/48076
See application file for complete search history.

(56) References Cited

U.S. PATENT DOCUMENTS 6,692,724 B1  2/2004  Yang et al.

FOREIGN PATENT DOCUMENTS

WO  WO 2010/057154 A1  5/2010
WO  WO 2010/083104 A2  7/2010
WO  WO 2011/079227 A1  6/2011

OTHER PUBLICATIONS

Christian Dohmen et al; Nanosized multifunctional Polyplexes for Receptor-Mediated SiRNA Delivery; ACSNANO vol. 6, No. 6, 2012, pp. 5198-5208.
Ying Liu et al; Synthesis and Evaluation of a Novel Lipophilic Folate Receptor Targeting Ligand; American Cancer Research; 2011; pp. 1521-1526.

*Primary Examiner* — Benjamin Packard
(74) *Attorney, Agent, or Firm* — Lucas & Mercanti, LLP

(57) ABSTRACT

Novel $N_3S_1$ chelator-folate derivatives, a preparation method thereof, and a composition for diagnosis and treatment of tumor including the same as an active ingredient are provided. The novel $N_3S_1$ chelator-folate derivatives or a pharmaceutically acceptable salt thereof are easily introduced into the cells using receptor binding to tumor expressing α-folate receptor (α-FR). Accordingly, the folate derivatives, labeled with radioisotope such as technetium, or rhenium, can be advantageously used for the diagnosis and treatment of tumor using tumor imaging and irradiation from the isotope, and therefore, can be widely used for the purpose of labeling a variety of radiopharmaceuticals.

13 Claims, 8 Drawing Sheets

N₃S₁ CHELATOR-FOLATE DERIVATIVES, PREPARATION METHOD THEREOF AND COMPOSITION FOR DIAGNOSIS OR TREATMENT OF CANCER CONTAINING THE SAME AS AN ACTIVE INGREDIENT

CROSS-REFERENCE TO RELATED APPLICATIONS

This application claims priority from Korean Patent Application No. 10-2012-0119743, filed on Oct. 26, 2012, and Korean Patent Application No. 10-2013-0127479, filed Oct. 25, 2013, in the Korean Intellectual Property Office, the contents of each of which are incorporated herein by reference in its entirety.

BACKGROUND

1. Field of the Invention

The present invention relates to novel $N_3S_1$ chelator-folate derivatives, preparation method thereof and composition for diagnosis or treatment of cancer containing the same as an active ingredient.

2. Description of the Related Art

Folate is introduced into a cell by the RFC (Reduced Folate Carrier) or folate receptor-mediated endocytosis, and generally, α-Folate receptor (α-FR) is overexpressed in a variety of cancer types such as ovarian, endometrial, breast, lung, renal, colorectal, nasopharyngeal and colon cancer, while it is present only locally in kidney or lung that stores and uses vitamins in the case of normal cells.

Folate is most frequently expressed in certain cancer type such as ovarian carcinoma and endometrial carcinoma, and is found to be expressed in more than 90% of cancer patients. Accordingly, many attempts targeting on overexpressed α-FR in cancers have been made to more effectively deliver the drug to the cancer cells and image the cancer.

α-FR is known as the membrane bound tumor-related antigen with high affinity, and it is the GPI (glycosylphosphatidylinositol) conjugated with 38 to 40 kDa membrane glycoprotein. α-FR binds with high affinity to folic acid, and the α-isoform α-FR has very low dissociation constant ($K_d$) with folic acid (approximately 0.1 nM), and has approximately 10 times lower dissociation constant than that of the reduced type of folates such as derivative of 5-methyltetrahydrofolate.

Meanwhile, folic acid, which is the compound having high affinity to folate receptor can maintain receptor binding property when combined by covalent bonding via γ-carboxyl group.

Recently, noninvasive imaging diagnostic agent for α-FR positive renal cell and ovarian carcinoma, which is diagnostic, radioisotope-labeled folate derivative, has successfully completed clinical phases I and II.

The noninvasive imaging method for selectively targeting tumors can accurately locate the primary lesion or tumor in the surgery, locate metastatic lesion and determine clinical stage, or observe reaction after treatment and find reoccurrence lesion.

Accordingly, it will be beneficial if it is possible to target a tumor noninvasively for the purpose of selective diagnosis or treatment, using radioisotopes.

The present inventors have been studied ways to synthesize substances to diagnose and treat α-folate receptor positive tumors in a noninvasive manner, by effectively targeting α-FR and the tumor, and were able to develop candidate substances that can effectively diagnose and treat the tumors, with positive α-folate receptor (α-FR) characteristic, by synthesizing folate derivative and introducing $N_3S_1$ chelator that can label radioisotope for diagnosis and treatment purposes, and completed the present invention.

SUMMARY OF THE INVENTION

An object of the present invention is to provide novel $N_3S_1$ chelator-folate derivative or a pharmaceutically acceptable salt thereof.

It is another object of the present invention to provide a preparation method of said novel $N_3S_1$ chelator-folate derivative or a pharmaceutically acceptable salt thereof.

It is yet another object of the present invention to provide complex of said novel $N_3S_1$ chelator-folate derivative and radioisotope.

It is yet another object of the present invention to provide a composition for the diagnosis and treatment of cancer, comprising said complex of the novel $N_3S_1$ chelator-folate derivative said radioisotope as an active ingredient.

It is yet another object of the present invention to provide a kit to form said complex of the novel $N_3S_1$ chelator-folate derivative and radioisotope.

In order to achieve the objects mentioned above, the present invention provides novel $N_3S_1$ chelator-folate derivative expressed by chemical formula 1 or a pharmaceutically acceptable salt thereof.

[Chemical formula 1]

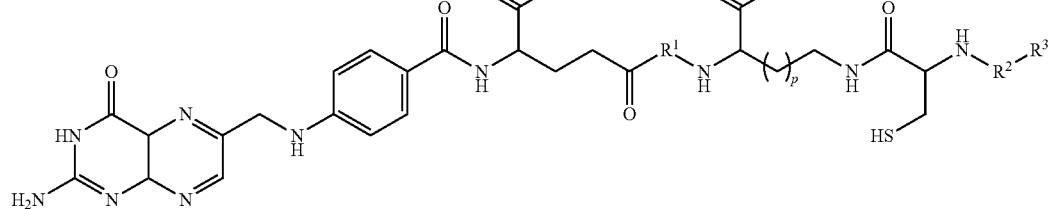

wherein, R, $R^1$, $R^2$, $R^3$ and p are as defined herein.

Further, the present invention provides a preparation method of the novel $N_3S_1$ chelator-folate derivative or a pharmaceutically acceptable salt thereof.

Further, the present invention provides a complex of the novel $N_3S_1$ chelator-folate derivative with radioisotope.

Further, the present invention provides a composition for diagnosis and treatment of cancer, comprising a complex of the novel $N_3S_1$ chelator-folate derivative and radioisotope as an active ingredient.

Further, the present invention provides a kit to form a complex of the novel $N_3S_1$ chelator-folate derivative and radioisotope.

In various embodiments, novel $N_3S_1$ chelator-folate derivative or a pharmaceutically acceptable salt thereof can be efficiently introduced into a cell using receptor conjugation to a tumor such as ovarian carcinoma expressing α-folate receptor (α-FR). Accordingly, the folate derivative can be labeled with radioisotope such as technetium or rhenium and advantageously used for the purpose of imaging tumor, or diagnosis and treatment of tumor using radiation emitted from the isotope. Therefore, the embodiments can be advantageously used for the purpose of labeling a variety of radiopharmaceuticals.

BRIEF DESCRIPTION OF THE DRAWINGS

The foregoing and/or other aspects according to an embodiment will be more apparent upon reading the description of certain exemplary embodiments with reference to the accompanying drawings, in which.

DETAILED DESCRIPTION OF EXEMPLARY EMBODIMENTS

Figure 1:
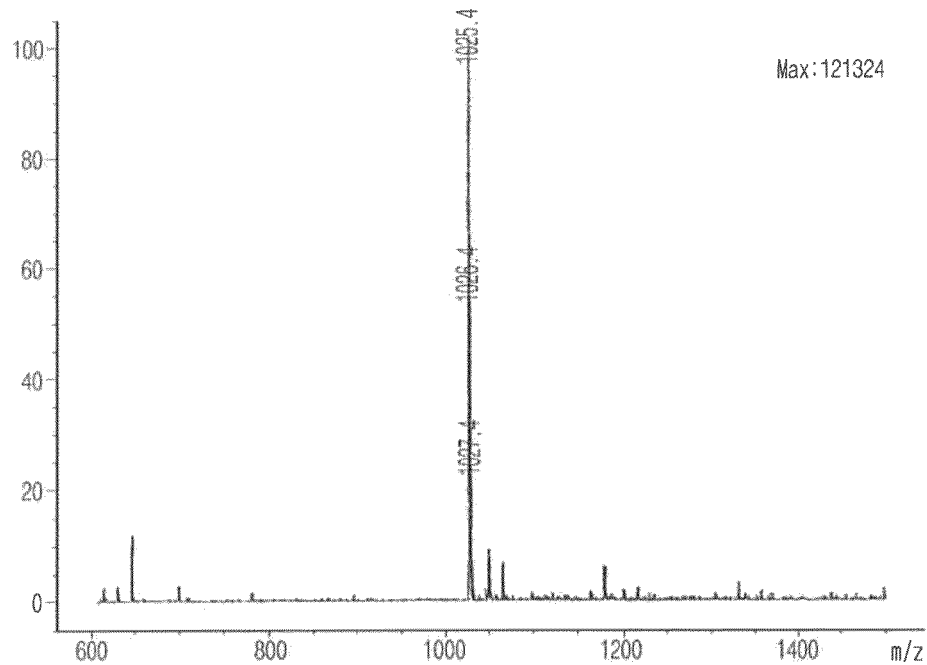
FIG. 1 shows PKCK-fol according to Example 1, which is the novel $N_3S_1$ chelator-folate derivative, analyzed by LC/MS, according to the present invention.

The present invention will be explained below with reference to embodiments and drawings.

The present invention provides novel $N_3S_1$ chelator-folate derivative expressed by Chemical Formula 1 below.

[Chemical Formula 1]

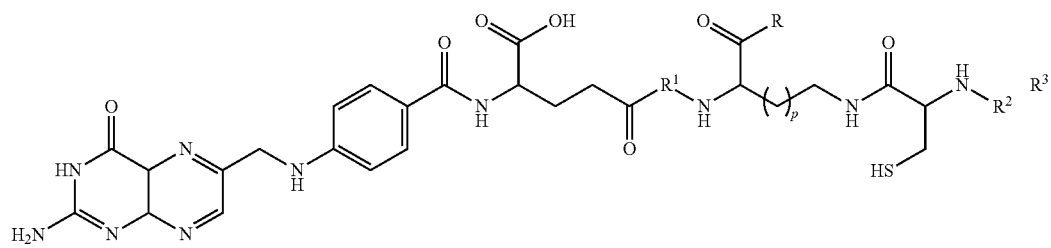

wherein, R is hydroxy or amine;

$R^1$ is nonbonding,

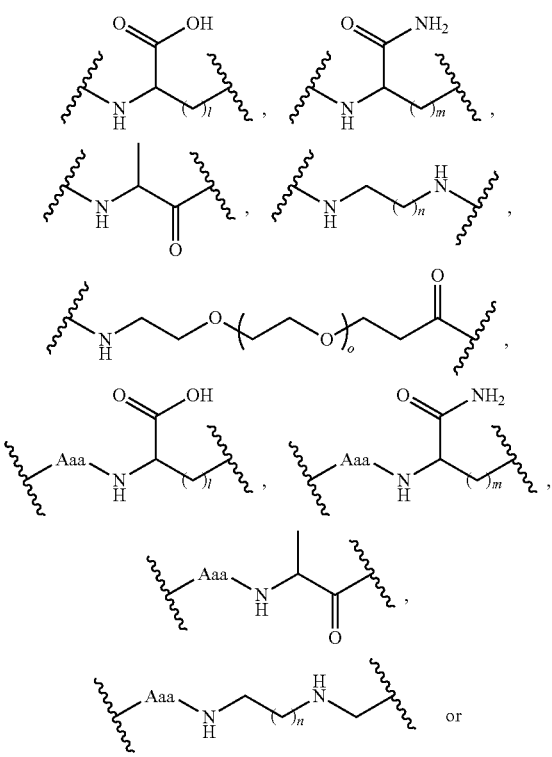

-continued

[Structure: Aaa-NH-CH2CH2-O-(CH2CH2O)o-C(=O)-]

in
which Aaa is selected from 1 to 3 amino acids, D-form amino acid, and derivative thereof;
L is an integer between 1 and 10;
m is an integer between 1 and 10;
n is an integer between 1 and 10;
o is an integer between 1 and 20;
$R^2$ is amino acid selected from a group consisting of alanine, arginin, asparagine, aspartic acid, cystine, glutaric acid, glutamine, glycine, histidine, iso-leucine, leucine, lysine, methionine, phenylalanine, proline, serine, threonine, tryptophan, tyrosine and valine;
$R^3$ is

[Structures shown: piperidine, pyrrolidine, substituted pyrrolidine with $R^4$, thiazolidine, dihydropyrrole, glycine with H2N, glycine with $R^5$-NH, or glycine with $R^5$-N-$R^5$]

$R^4$ is halogen, hydroxy, amine;
$R^5$ is alkyl between $C_1$ and $C_4$; and
p is an integer between 1 and 10.

In a preferred embodiment,
R is hydroxyl or amine;
$R^1$ is nonbonding,

[Structures shown with -COOH, -CONH2, methyl, and ethylenediamine linkers]

-continued

[Structure: NH-CH2CH2-O-(CH2CH2O)o-C(=O)-]

[Structures shown with -COOH (subscript l), -CONH2 (subscript m), methyl, ethylenediamine (subscript n)]

[Structure: Aaa-NH-CH2CH2-O-(CH2CH2O)o-C(=O)-]

in which Aaa is any one selected from 1 to 3 amino acids, D-form amino acid, and derivative thereof;
l is an integer between 1 and 4;
m is an integer between 1 and 4;
n is an integer between 1 and 6;
o is an integer between 1 and 10;
$R^2$ is amino acid selected from a group consisting of alanine, arginin, asparagine, aspartic acid, cystine, glutaric acid, glutamine, glycine, histidine, iso-leucine, leucine, lysine, methionine, phenylalanine, proline, serine, threonine, tryptophan, tyrosine and valine;
$R^3$ is

[Structures shown: piperidine, pyrrolidine, substituted pyrrolidine with $R^4$, thiazolidine, dihydropyrrole, glycine with H2N, glycine with $R^5$-NH, or glycine with $R^5$-N-$R^5$]

$R^4$ is fluoro, hydroxy, amine;
$R^5$ is methyl or ethyl; and
p is an integer between 1 and 4.

The novel $N_3S_1$ chelator folate derivative expressed by Chemical Formula 1 according to the present invention may be used in the form of pharmaceutically acceptable salt, in which case acid addition salt formed by a pharmaceutically acceptable free acid can be advantageously used as the salt. The expression "pharmaceutically acceptable salt" refers to any organic or inorganic addition salt of basic compound of Chemical Formula 1, at a concentration that gives effective action that is relatively non-toxic to a patient and has effective action that is harmless, with adverse side effect thereof within a range that does not affect the beneficial efficacy of the basic compound of Chemical Formula 1. These salts may use inorganic and organic acids as the free acids, in which the inorganic acid may include hydrochloric acid, hydrobromic acid, nitric acid, sulfuric acid, perchloric acid, or phosphoric acid, and the organic acid may include citric acid, acetic acid, lactic acid, maleic acid, fumaric acid, gluconic acid, methane sulfonic acid, glycol acid, succinic acid, tartaric acid, galactronic acid, embonic acid, glutamic acid, aspartic acid, oxalic acid, (D) or (L) malic acid, maleic acid, methane sulfonic acid, ethane sulfonic acid, 4-toluene sulfonic acid, salicylic acid, citric acid, benzoic acid or malonic acid. Further, these salts may include alkali metal salt (e.g., sodium salt, potassium salt, etc.) and alkali earth metal salt (e.g., calcium salt, magnesium salt, etc.). For example, the acid addition salt may include acetate, aspartate, benzoate, besylate, bicarbonate/carbonate, bisulfate/sulfate, borate, camsylate, citrate, edisilate, esylate, formate, fumarate, gluceptate, gluconate, glucuronate, hexafluorophosphate, hibenzate, hydrochloride/chloride, hydro-bromide/bromide, hydroiodide/iodide, isethionate, lactate, malate, maleate, malonate, mesylate, methyl sulfate, naphthyl acrylate, 2-naphsylate, nicotinate, nitrate, orotate, oxalate, palmitate, pamoate, phosphate/hydrogen phosphat/dihydrogen phosphate, saccharate, stearate, succinate, tartrate, tosylate, trifluoro acetate, aluminum, arginine, benzathine, calcium, choline, diethylamine, diolamine, glycine, lysine, magnesium, meglumine, alamine, potassium, sodium, tromethamine, or zinc salt, or preferably, hydrochloride or trifluoromethyl acetate.

Further, the novel $N_3S_1$ chelator-folate derivative expressed by Chemical Formula 1 according to the present invention may include not only the pharmaceutically acceptable salt, but also all the salts, isomers, hydrate and solvate.

The addition salt according to the present invention may be prepared in the conventional manner by, for example, melting the compound of Chemical Formula 1 in water-miscible organic solvent, such as acetone, methanol, ethanol, or acetonitrile., adding excess organic acid or adding acid solution of organic acid for precipitating or crystallization. After that, addition salt may be obtained by evaporating the solvent or excess acid and drying, or by suction-filtering the salt precipitate.

Further, the present invention provides a preparation method of novel $N_3S_1$ chelator-folate derivative, which includes steps as expressed by Reaction Formula 1 below, reacting the folic acid derivative of Chemical Formula 2 with a compound of Chemical Formula 3, to prepare the folate derivative of Chemical Formula 4 (step 1); and preparing the compound of Chemical Formula 1 by eliminating resin, a solid phase support of the folate derivative of Chemical Formula 4 prepared at step 1, under acidic condition.

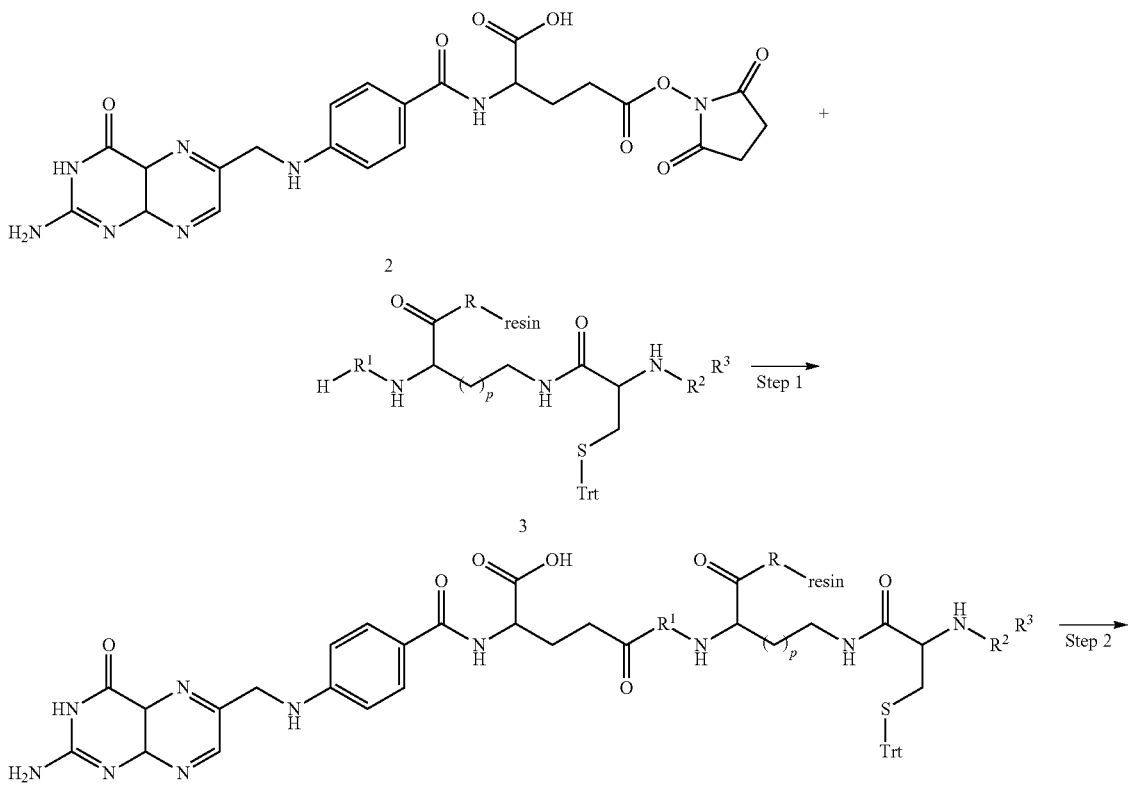

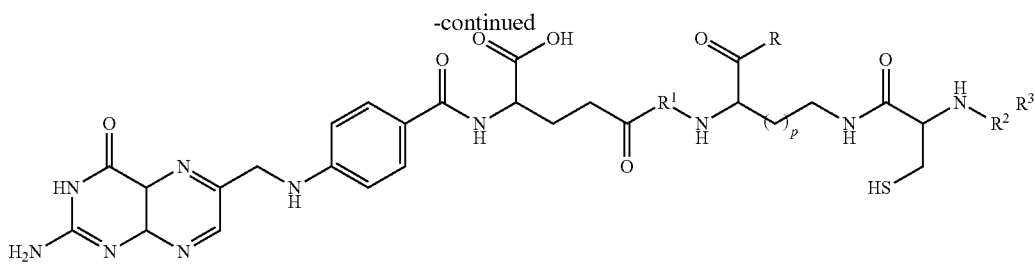

wherein, R, $R^1$, $R^2$, $R^3$ and p are as defined by Chemical Formula 1 above; resin is a solid phase support; and Trt is trityl group.

Hereinbelow, the preparation method will be explained step by step.

First, in one embodiment, step 1 involves coupling reaction of the folic acid derivative and the compound of Chemical Formula 3, in which benzoester group of the folic acid derivative is combined with terminal amine of the compound of Chemical Formula 3, to give the compound expressed by Chemical Formula 4.

The coupling reaction may use diisopropylamine or triethylamine, along with amide coupling reagent such as benzotriazol-1-yl-oxy-tris(dimethylamino)-phosphonium hexafluorophosphate (Py-BOP), O-benzotriazol-N,N,N',N'-tetramethyl-uronium-hexafluoro-phosphate (HBTU), 2-(7-aza-1H-benzotriazol-1-yl)-1,1,3,3-tetramethyluronium hexafluorophosphate (HATU), hydroxybenzotriazol (HOBt), dicyclohexylcarbodiimide (DCC), 1-ethyl-3-(3-dimethylaminopropyl)carbodiimide (EDC), or carbonyldiimidazol (CDI), or preferably, hydroxybenzotriazol (HOBt) and/or O-benzotriazol-N,N,N',N'-tetramethyl-uronium-hexafluorophosphate (HBTU).

Further, the organic solvent that does not affect the reaction may be used for the reaction, such as, methanol, dimethylformamide (DMF), dimethylsulfoxide (DMSO), tetrahydrofuran, dichloromethane, or toluene, or preferably, dimethylsulfoxide (DMSO) or dimethylformamide (DMF).

Next, step 2 according to the present invention involves eliminating resin as solid phase support and protecting group of the compound of Chemical Formula 4 prepared at step 1.

To remove the resin, it is preferably to use a mixture or TFA (Trifluoroacetic acid), TIS, EDT, thioanisole and water, and for effective removal of resin, the mixture rate of TFA, TIS, EDT, thioanisole and water is preferably TFA:TIS:EDT:thioanisole:water=90-92:2.0-2.5:2.0-2.5:2.0-2.5:2.0-2.5.

Further, the present invention provides a preparation method of a compound expressed by Chemical Formula 3 of the Reaction Formula 1, which may include steps as expressed in Reaction formula 2 below, preparing a compound expressed, by Chemical formula by reacting lysine protected by alloc protecting group with cysteine protected by Fmoc protecting group (step 1);

preparing a compound expressed by Chemical Formula 7 by reacting the compound of Chemical formula 5 prepared at step 1 with compound expressed by Chemical Formula 6 (step 2);

preparing a compound expressed by Chemical Formula 9 by reacting the compound of Chemical Formula 7 prepared at step 2 with compound expressed by Chemical Formula 8 (step 3); and preparing a compound expressed by Chemical formula 3 by reacting the compound of Chemical Formula 9 prepared at step 3 with compound expressed by Chemical Formula 10 (step 4).

[Reaction Formula 2]

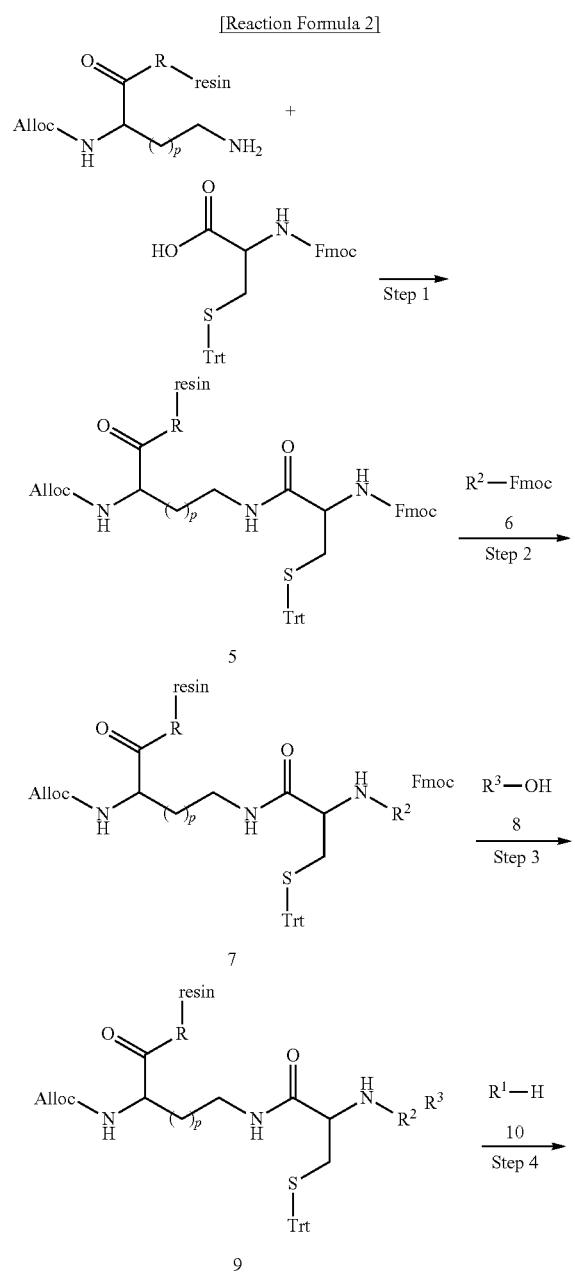

-continued

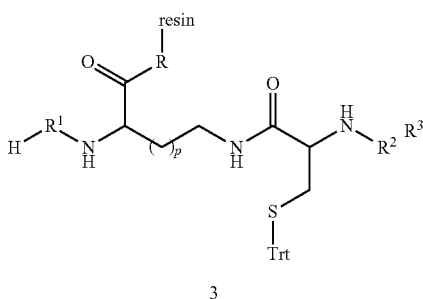

3 wherein, R, $R^1$, $R^2$, $R^3$ and p are as defined in the Chemical Formula 1; resin is solid phase support; Alloc is allylcarbamate; Fmoc as fluorenylmethyloxycarbonyl group; and Trt is trityl group.

The preparation method will be explained in detail below by referring to each step.

First, step 1 according to one embodiment involves preparation of compound expressed by Chemical Formula 5 by reacting lysine protected by alloc protecting group with cysteine protected by Fmoc protecting group, in which terminal amine couples the other terminal amine protected with Alloc protecting group of lyine, with carboxylic acid of cysteine whose terminal amine is protected with Fmoc protecting group and thiol is protected with Trt protecting group.

The coupling reaction may use diisopropylethylamine or triethylamine, along with amide coupling reagent such as benzotriazol-1-yl-oxy-tris(dimethylamino)-phosphonium hexafluorophosphate (Py-BOP), O-benzotrizol-N,N,N',N'-tetramethyl-uronium-hexafluoro-phosphate (HBTU), 2-(7-aza-1H-benzotriazol-1-yl)-1,1,3,3-tetramethyluronium hexafluorophosphate (HATU), hydroxybenzotriazol (HOBt), dicyclohexylcarbodiimide (DCC), 1-ethyl-3-(3-dimethylaminopropyl)carbodiimide (EDC), or carbonyldiimidazol (CDI), or preferably, hydroxybenzotriazol (HOBt) and/or O-benzotriazol-N,N,N',N'-tetramethyl-uronium-hexafluoro-phosphate (HBTU).

Further, for the possible organic solvent to use, methanol, dimethylformamide, dimethylsulfoxide, tetrahydrofuran, dichloromethane, or toluene, which do not affect the reaction, may be need, or preferably, dimethylsulfoxide or dimethylformamide may be used.

Next, step 2 according to the present invention involves preparation of a compound expressed by Chemical Formula 7, by reacting the compound of Chemical Formula 5 prepared at step 1 with compound of Chemical Formula 6, in which the Fmoc protecting group is removed from the protected terminal amine of the compound expressed by Chemical Formula 5 prepared at step 1, and the deprotected terminal amine is coupled with the compound of Chemical Formula 6, to give the compound of Chemical Formula 7.

Generally known methods may be used to remove the Fmoc protecting group from Chemical Formula 5 in step 2.

Further, the reaction is performed under the conditions as explained above with reference to step 1.

Next, according to the present invention, step 3 involves preparing a compound expressed by Chemical Formula 9 by reacting the compound of Chemical Formula 7 prepared at step 2 with compound of expressed by Chemical Formula 8, in which Fmoc protecting group is removed from the protected terminal amine of the compound expressed by Chemical Formula 7 prepared at step 2, and the deprotected terminal amine is coupled with the compound expressed by Chemical Formula 8 protected with Fmco protecting group, to give the compound of Chemical Formula 9.

Generally known methods may be used to remove the Fmoc protecting group from Chemical Formula 7 in the above step.

Further, the reaction may be performed under the same conditions as those explained above with reference to step 1.

Next, according to the present invention, step 4 involves preparation of a compound expressed by Chemical Formula 3, by reacting the compound of Chemical Formula 9 prepared at step 3 with compound expressed by Chemical Formula 9, in which Alloc protecting group is removed from the protected terminal amine of the compound expressed by Chemical Formula 9 prepared at step 3, and the deprotected terminal amine is coupled with compound of Chemical Formula 10 to give the compound expressed by Chemical Formula 3.

Generally known methods nay be used to remove the Alloc protecting group from Chemical Formula 9 in the above step.

Further, the reaction may be performed under the same conditions as those explained above with reference to step 1.

Further, as represented by Reaction Chemical 3 below, the present invention provides a preparation method or novel $N_3S_1$ chelator-folate derivative, which may include:

preparing folate derivative of Chemical Formula 4 by reacting pteroic acid derivative of Chemical Formula 11 with compound of Chemical Formula 12 (step 1); and preparing compound of Chemical Formula 1 by removing resin, solid phase support of the folate derivative of Chemical Formula 4 prepared at step 1, under acidic condition (step 2).

[Reaction Formula 3]

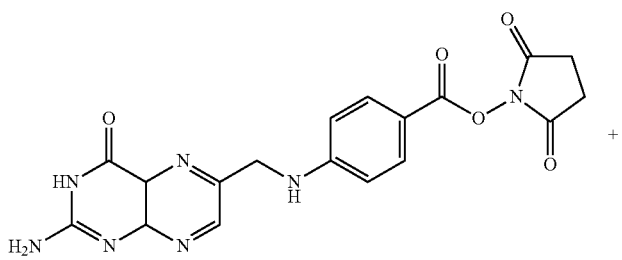

11

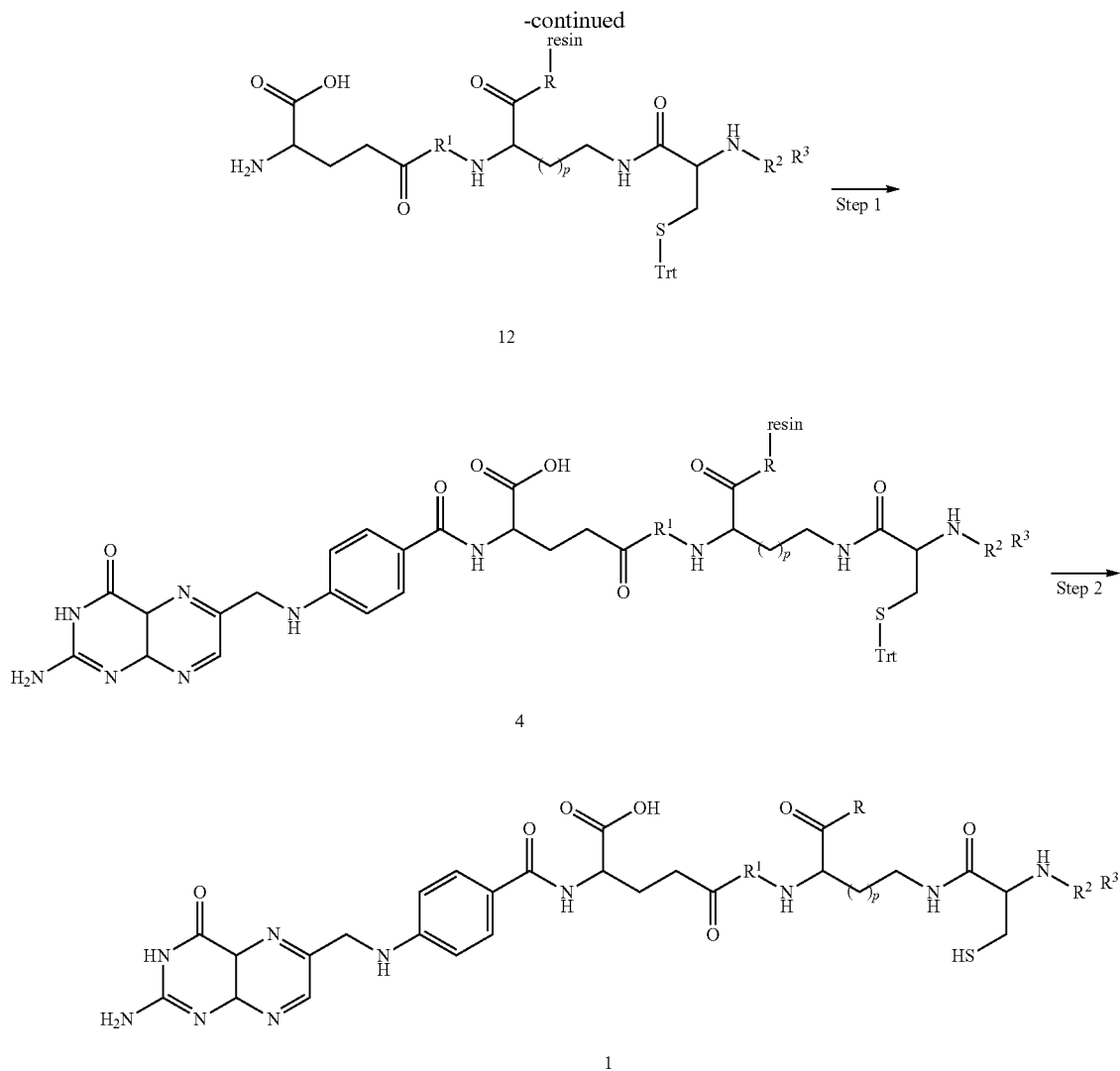

wherein, R, $R^1$, $R^2$, $R^3$ and p are as defined in Chemical Formula 1; resin is solid phase support; and Trt is trityl group.

Hereinbelow, the preparation method will be explained step by step.

First, step 1 according to the present invention involves coupling folic acid derivative expressed by Chemical Formula 11 with compound expressed by Chemical Formula 12, in which benzoester group of the folic acid derivative of Chemical Formula 11 is coupled with terminal amine of compound of Chemical Formula 12, to give compound expressed by Chemical Formula 4.

The coupling reaction may use diisopropylethylamine or triethylamine, along with amine coupling reagent such as benzotriazol-1-yl-oxy-tris(dimethylamino)-phosphonium hexafluorophosphate (Py-BOP), O-benzotriazol-N,N,N',N'-tetramethyl-uronium-hexafluoro-phosphate (HBTU), 2-(7-aza-1H-benzotriazol-1-yl)-1,1,3,3-tetramethyluronium hexafluorophosphate (HATU), hydroxybenzotriazol (HOBt), dicyclohexylcarbodiimide (DCC), 1-ethyl-3-(3-dimethylaminopropyl)carbodiimide (EDC, or carbonyldiimidazol (CDI), or preferably, hydroxybenzotriazol (HOBt) and/or O-benzotriazol-N,N,N',N'-tetramethyl-uronium-hexafluorophosphate (HBTU).

Further, for the possible organic solvent to use, methanol, dimethylformamide, dimethylsulfoxide, tetrahydrofuran, dichloromethane, or toluene which do not affect the reaction, may be used, or preferably, dimethylsulfoxide or dimethylformamide may be used.

Next, according to the present invention, step 2 removes resin, the solid phase support of compound of Chemical Formula 4 prepared at step 1, and protecting group.

To remove the resin, it is preferable to use a mixture of TFA (Trifluoroacetic acid), TIS, EDT, thioanisole (Thioanisole) and water, and preferably at a ratio of TFA:TIS:EDT:thioanisole:water=90-92: 2.0-2.5:2.0-2.5:2.0-2.5:2.0-2.5 to ensure effective removal of resin.

Further, as represented by Reaction Formula 4 below, the present invention provides a preparation method of novel $N_3S_1$ chelator-folate derivative, which may include;

preparing a compound expressed by Chemical Formula 14, by coupling compound expressed by Chemical Formula 3 with glutamic acid expressed by Chemical Formula 13 (step 1); and preparing compound expressed by Chemical Formula 12 by deprotecting the compound of Chemical Formula 14 prepared at step 1 (step 2).

[Reaction Formula 4]

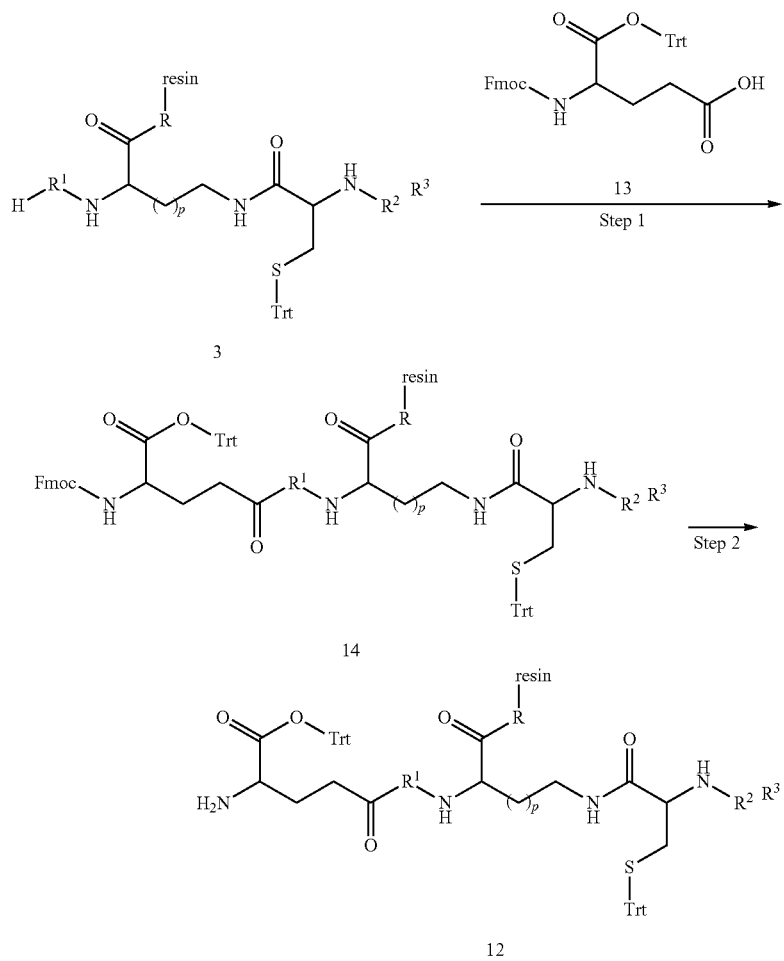

wherein, R, $R^1$, $R^2$, $R^3$ and p are as defined in Chemical Formula 1; resin is solid phase support; Fmoc is fluorenylmethyloxycarbonyl group 이고; and Trt is trityl group.

Hereinbelow, the preparation method will be explained step by step.

First, step 1 according to present invention involves preparing compound expressed by Chemical Formula 14 by coupling the compound expressed by Chemical Formula 3 with glutamic acid expressed by Chemical Formula 13, in which terminal end $R^1$ of the compound expressed by Chemical Formula 3 is coupled with carboxylic acid of glutamic acid of Chemical Formula 13.

For the coupling reaction, diisopropylethylamine or triethylamine, along with amide coupling reagent such as benzotriazol-1-yl-oxy-tris(dimethylamino)-phosphonium hexafluorophosphate (Py-BOP), O-benzotriazol-N,N,N',N'-tetramethyl-uroniuin-hexafluoro-phosphate (HBTU), 2-(7-aza-1H-benzotriazol-1-yl)-1,1,3,3-tetramethyluronium hexafluorophosphate (HATU), hydroxybenzotriazol (HOBt), dicyclohexylcarbodiimide (DCC), 1-ethyl-3-(3-dimethylaminopropyl)carbodiimide (EDC), or carbonyldiimidazol (CDI) may be used, or preferably, hydroxybenzotriazol (HOBt) and/or O-benzotriazol-N,N,N',N'-tetramethyl-uronium-hexafluoro-phosphate (HBTU) may be used.

Further, for the possible organic solvent to use, methanol, dimethylformamide, dimethylsulfoxide, tetrahydrofuran, dichloromethane, or toluene, which do not affect the reaction, may be used, or preferably, dimethylsulfoxide or dimethylformamide may be used.

Next, according to the present invention, step 2 involves preparing compound of Chemical Formula 7 by reacting the compound of Chemical Formula 5 prepared at step 1 with compound of Chemical Formula 6, in which Fmoc protecting group is removed from the protected terminal amine of the compound expressed by Chemical Formula 5 prepared at step 1 and the deprotected terminal amine is coupled with the compound of Chemical Formula 6 to give the compound of Chemical Formula 7.

Next, according to the present invention, step 2 involves preparing a compound expressed by Chemical Formula 12 by deprotecting the compound expressed by Chemical Formula 14 prepared at step 1, in which the protected terminal amine of the compound expressed by Chemical Formula 14 prepared at step 1 is deprotected.

Generally known methods may be used to remove the Fmoc protecting group from Chemical Formula 5 in the above step.

According to the preparation method of folate derivative of the present invention, resin, which is the solid phase support, is coupled with the carboxylic group of amino acid introduced into folate derivative, and preferably may use Wang resin or Merrifield resin (MBHA).

When the Wang resin is used, de-coupling the resin causes hydroxyl group to be introduced into R of Chemical Formula 1, while when Merrifield resin (MBHA resin) is used, de-coupling resin causes introduction of amine group.

[Chemical formula 1]

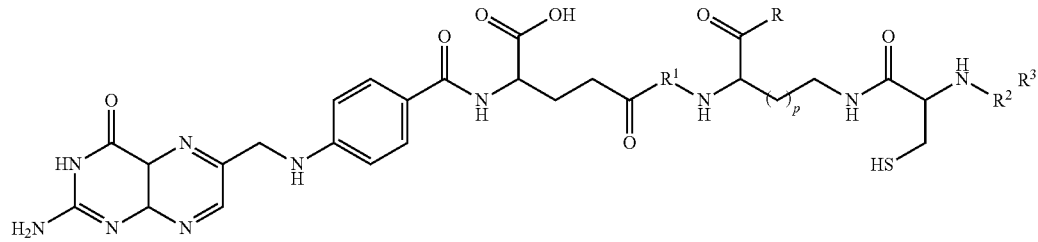

wherein, R, $R^1$, $R^2$, $R^3$ and p are as defined in Chemical formula 1.

Further, the present invention provides radioisotope-labeled, novel $N_3S_1$ chelator-folate.

According to the present invention, the radioisotope-labeled, novel $N_3S_1$ chelator-folate includes metal and transition metal with properties that can be detected with MRI, CT or gamma camera when present in living organism, and radioisotope to emit radioactive rays. For example, the radioisotope may be selected from a group consisting of scandium-47 (Sc-47), copper-64 (Cu-64), gallium-67 (Ga-67), gallium-68 (Ga-68), yttrium-86 (Y-86), yttrium-90 (Y-90), technetium-93m (Tc-99m), indium-111 (In-111), promethium-149 (Pm-149), samarium-153 (Sm-153), dysprosium-165 (Dy-165), holmium-166 (Ho-166), erbium-169 (Er-169), lutetium-177 (Lu-177), rhenium-186 (Re-186), rhenium-188 (Re-188) and bismuth-212 (Bi-212). Preferably, technetium-99m (Tc-99m), rhenium-186 (Re-186) or rhenium-188 (Re-188) may be used.

Further, the present invention provides a preparation method of a radioisotope-labeled novel $N_3S_1$ chelator-folate derivative.

The radioisotope may be labeled on the novel $N_3S_1$ chelator-folate derivative by transchelation, using glucoheptonate (GH), gluconate, EDTA, tartrate, or pyrophosphate as ligand exchange reaction kit.

As a result, the prepared radioisotope-labeled novel $N_3S_1$ chelator-folate derivative may be produced with high yield exceeding 98% even at a concentration of 1 nmol without requiring purification process (Example 8).

Further, the present invention provides a composition for diagnosis or treatment of cancer, comprising the novel $N_3S_1$ chelator-folate derivative and radioisotope as an active ingredient.

As a result, the prepared novel $N_3S_1$ chelator-folate derivative has good radiochemical purity (RCP 98% or above) and high labeling efficiency of 37 GBq/umol (see FIG. 2), good in vitro stability of 96% or above (see FIG. 3), and cell affinity and internalization rate which increase time-dependently (see FIG. 4), and therefore, can be advantageously used for the diagnosis of cancer using medical imaging equipments or treatment of cancer using energy emitted from radioisotope.

When used as a medical product, a pharmaceutical composition according to the present invention containing the radioisotope-labeled, novel $N_3S_1$ chelator-folate or a pharmaceutically acceptable salt thereof as an active ingredient may be formulated and administered in clinical phase, but not limited thereto.

The pharmaceutical composition containing a complex, which is prepared by labeling the derivative expressed by Chemical Formula 1 with radioisotope, as an active ingredient may be prepared for parenteral administration, and the parenteral administration may be done by subcutaneous injection, intravenous injection, intramuscular injection or intrathoracic injection.

For formulation into a dosage form for parenteral administration, the radioisotope-labeled, novel $N_3S_1$ chelator-folate or pharmaceutically acceptable salt thereof is mixed with stabilizer or buffer in water into solution or suspension, which may then be prepared into ampoule or vial unit dosage form. The composition may be sterilized and/or many contain adjurvants such as preservatives, stabilizers, wetting or oil promoter, salt for osmoregulation and/or buffer, and other therapeutically useful matters, and may be prepared by conventional mixing, granulation or coating process.

The dose of the pharmaceutical composition containing the radioisotope-labeled folate novel $N_3S_1$ chelator as an active ingredient to human body depends on age, weight, gender, dosage forms, health condition and severity or disease, said preferably, the pharmaceutical composition may be administered in an amount of 0.01 to 200 mg/kg/day at predetermined time intervals for several times, or preferably, for one to three times a day, by oral or parenteral route.

Further, the present invention provides a kit to form complex of the novel $N_3S_1$ chelator-folate derivative and radioisotope. To be specific, the kit may be used for the purpose of preparing radiopharmaceutical products labeled with technetium or rhenium in sterile nonpyrogenic form, and for convenience of technetium or rhenium labeling using complex compound of the novel $N_3S_1$ chelator-folate derivative and radioisotope, the novel $N_3S_1$ chelator-folate derivative and proper buffer solution are added in liquid state in advance, and seeded on a pharmaceutically-acceptable sterile vial and sealed for use, or preserving by cooling, freezing or freeze-drying for later use.

Hereinbelow, examples and experimental examples according to the present invention will be explained in detail.

However, the following examples are only provided for the illustrative purpose, and the present invention is not limited to any of the examples.

PREPARATIVE EXAMPLE 1

Preparation of Folic Acid Derivative

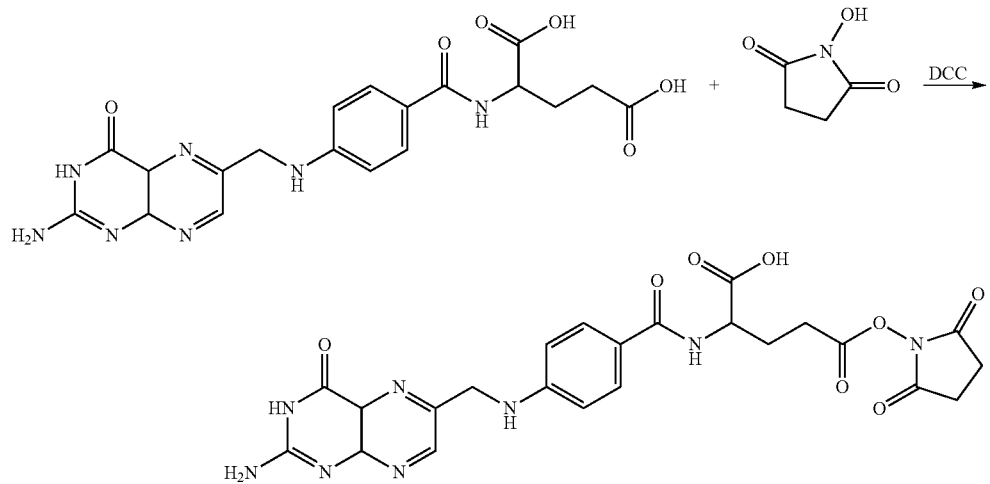

The folic acid derivative expressed by Chemical Formula 2 may be synthesized as expressed by Reaction Formula 5 above by the generally known methods in the organic synthesis field, or commercially available one may be used.

PREPARATIVE EXAMPLE 2

Preparation of Pteroic Acid Derivative

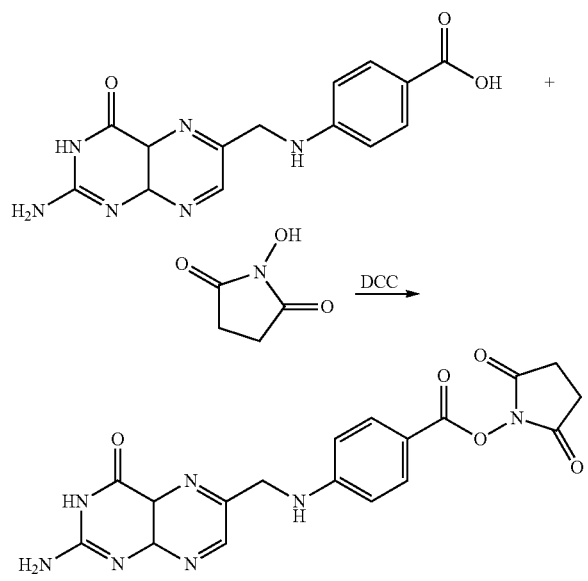

The pteroic acid derivative expressed by Chemical Formula 12 may be synthesized as expressed by Reaction Formula 6 above by the generally known methods in the organic synthesis field, or commercially available one may be used.

PREPARATIVE EXAMPLE 3

Preparation of P(Boc)-K(Boc)-C(Trt)-K-Wang Resin

Wang resin was washed with dimethylformamide (DMF), and washed with 1.0M hydroxybenzotriazol solution (HOBt, dimethylformamide solution). After dissolution with Alloc-Lys(Fmoc)-OH (1 mmol), hydroxybenzotriazol (3 mmol), O-benzotriazol-N,N,N',N'-tetramethyl-uronium-hexafluoro-phosphate (HBTU, 3 mmol), and diisopropylethylamine (6 mmol) in dimethylformamide, stirring for 2 hr followed. The resin was washed with dimethylformamide, dichloromethane, and dimethylformamide in order, dissolved in dimethylformamide solution containing 20% piperidine, and then stirred for 10 min. After the stirring, washing with dimethylformamide followed. Next, the resin was dissolved with Fmoc-Cys(Trt)-OH (3 mmol), hydroxybenzotriazol (HOBt, 3 mmol), O-benzotriazol-N,N,N',N'-tetramethyl-uronium-hexafluoro-phosphate (HBTU, 3 mmol), and diisopropyl-ethylamine (6 mmol) in dimethylformamide, and stirred for 3 hr. After that, Lys(Boc)-OH and Pro(Boc)-OH, whose terminal amines are protected with Fmoc protecting group, were added in order for reaction. After the respective procedures, tetrakis(triphenylphosphine)palladium (0) and 1,3-dimethyl-barbituric acid were added to dichloromethane, followed by stirring for 2 hr and washing, which gave target compound without requiring separate purification.

PREPARATIVE EXAMPLE 4

Preparation of P(Boc)-K(Boc)-C(Trt)-K-E(Trt)-Wang Resin

P(Boc)-K(Boc)-C(Trt)-K-Wang resin of Preparative Example 3 was dissolved in dimethylformamide, and added with Fmoc-Glu(Trt)-OH (3 mmol), hydroxybenzotriazol (HOBt, 3mmol), O-benzotriazol-N,N,N',N'-tetramethyl-uronium-hexafluoro-phosphate (HBTU, 3 mmol), and diisopropylethylamine (6 mmol). After stirring for 3 hr, the reactant was washed with dimethylformamide, dichloromethane, and dimethylformamide in order, which gave target compound without requiring separate purification.

PREPARATIVE EXAMPLE 5

Preparation of P(Boc)-K(Boc)-C(Trt)-K-E(Trt)-E(Trt)-Wang Resin

The target compound was obtained with the same method as that of Preparative Example 4, except for the difference of using P(Boc)-K(Boc)-C(Trt)-K-E(Trt)-Wang resin of Preparative Example 4, instead of P(Boc)-K(Boc)-C(Trt)-K-Wang resin.

PREPARATIVE EXAMPLE 6

Preparation of P(Boc)-(FITC)K(Boc)-C(Trt)-K-E(Trt)-Wang Resin

Step 1: Preparation of a P(Boc)-K(FITC)-C(Trt)-K-Wang Resin

The target compound was obtained with the same method as that of Preparative Example 3, except, for the difference of using Fmoc-Lys(Mtt)-OH removed of Mtt protecting group and added with FITC, instead of Alloc-Lys (Fmoc)-OH.

Step 2: Preparation of P(Boc)-(FITC)K(Boc)-C(Trt)-K-E(Trt)-Wang Resin

After dissolving P(Boc)-K(FITC)-C(Trt)-K-Wang resin of step 1 in dimethylformamide, Fmoc-Glu(Trt)-OH (3 mmol), hydroxybenzotriazol (HOBt, 3 mmol), O-benzotriazol-N,N,N',N'-tetramethyl-uronium-hexafluoro-phosphate (HBTU, 3 mmol), and diisopropylethylamine (6 mmol) were added. After stirring for 3 hr, the reactant was washed with dimethylformamide, dichloromethane, and dimethylformamide in order, which gave target compound without requiring separate purification.

PREPARATIVE EXAMPLE 7

Preparation of P(Boc)-S(t-Bu)-C(Trt)-K-(Beta-A)-E(Trt)-Wang Resin

After washing Wang resin with dimethylformamide (DMF), and washing with 1.0M hydroxybenzotriazol solution (HOBt, dimethylformamide solution), the Wang resin was dissolved with Alloc-Lys (Fmoc)-OH (1 mmol), hydroxybenzotriazol (3 mmol), O-benzotriazol-N,N,N',N'-tetramethyl-uronium-hexafluoro-phosphate (HBTU, 3 mmol), and diisopropylethylamine (6 mmol) in dimethylformamide. After stirring for 2 hr, the resin was washed with dimethylformamide, dichloromethane, and dimethylformamide in order, dissolved in dimethylformamide solution containing 20% piperidine, stirred for 10 min, and washed with dimethylformamide. Next, the resin was dissolved with Fmoc-(Beta-Ala)-OH (6 mmol), hydroxybenzotriazol (3 mmol), O-benzotriazol-N,N,N',N'-tetramethyl-uronium-hexafluoro-phosphate (HBTU, 3 mmol), and diisopropylethylamine (6 mmol) in dimethylformamide. After stirring for 3 hr, Cys(Trt)-OH, Ser(t-Bu)-OH, and Pro(Boc)-OH, whose terminal amines are protected with Fmoc protecting group, were added in order for reaction. After the respective procedures, tetrakis (triphenylphosphine)palladium(0) and 1,3-dimethylbarbituric acid were added to dichloromethane, followed by stirring for 2 hr and washing, which gave target compound without requiring separate purification.

PREPARATIVE EXAMPLE 8

Preparation of P(Boc)-D(t-Bu)-C(Trt)-K-(miniPEG)-E(Trt)-MBHA Resin

MBHA resin was washed with dimethylformamide (DMF), and then washed with 1.0M hydroxybenzotriazol solution (HOBt, dimethylformamide solution). The MBHA resin was then dissolved with Alloc-Lys (Fmoc)-OH (1 mmol), hydroxybenzotriazol (HOBt, 3 mmol), O-benzotriazol-N,N,N',N'-tetramethyl-uronium-hexafluoro-phosphate (HBTU, 3 mmol), and diisopropylethylamine (6 mmol) in dimethylformamide. After stirring for 2 hr, the resin was washed with dimethylformamide, dichloromethane, and dimethylformamide in order, dissolved in dimethylformamide solution containing 20% piperidine, stirred for 10 min, and washed with dimethylformamide. Next, the resin was dissolved with Fmoc-miniPEG-OH (3 mmol), hydroxybenzotriazol (3 mmol), O-benzotriazol-N,N,N',N'-tetramethyl-uronium-hexafluoro-phosphate (HBTU, 3 mmol), and diisopropylethylamine (6 mmol) in dimethylformamide. After stirring for 3 hr, Cys(Trt)-OH, Asp(t-Bu)-OH, and Pro(Boc)-OH, whose terminal amines are protected with Fmoc protecting group, were added in order for reaction. After the respective procedures, tetrakis (triphenylphosphine)palladium(0) and 1,3-dimethylbarbituric acid were added to dichloromethane, followed by stirring for 2 hr and washing, which gave target compound without requiring separate purification.

PREPARATIVE EXAMPLE 9

Preparation of P(Boc)-K(Boc)-C(Trt)-K-MBHA Resin

Target compound was obtained by the same method as that of Preparative Example 3, except for the difference of using MBHA resin instead of Wang resin.

PREPARATIVE EXAMPLE 10

Preparation of P(Boc)-K(Boc)-C(Trt)-K-E(Trt)-MBHA Resin

Target compound was obtained by the same method as that of Preparative Example 4, except for the difference of using P(Boc)-K(Boc)-C(Trt)-K-MBHA resin of Preparative Example 9 instead of P(Boc)-K(Boc)-C(Trt)-K-Wang resin.

EXAMPLE 1

Preparation of PKCK-Fol-OH 1

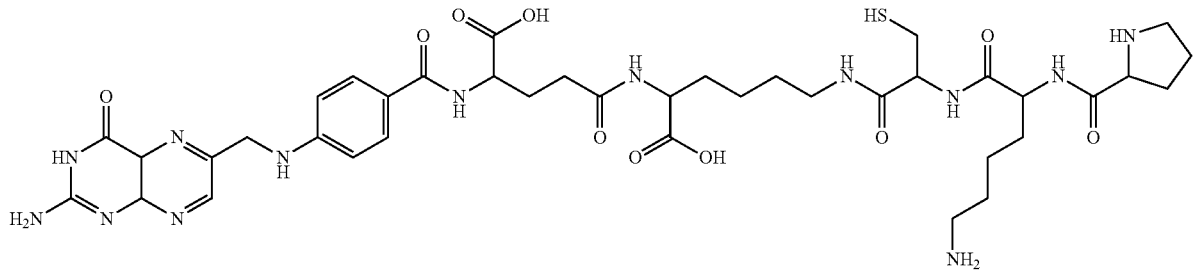 [SMILES: NCCCCC(NC(=O)C1CCCN1)C(=O)NC(CS)C(=O)NCCCCC(NC(=O)CCC(NC(=O)c1ccc(NCC2=NC3C(=O)NC(N)=NC3N=C2)cc1)C(=O)O)C(=O)O]

Step 1: Preparation of P(Boc)-K(Boc)-C(Trt)-K-Wang Resin-Fol

The folate derivative (1 mmol) of Preparative Example 1 or folate (1 mmol) was dissolved in dimethylsulfoxide (20 ml), followed by addition of P(Boc)-K(Boc)-C(Trt)-K-Wang resin (0.3 moll) of Preparative Example 3, hydroxybenzotriazol (HOBt, 1 mmol), O-benzotriazol-N,N,N',N'-tetramethyl-uronium-hexafluoro-phosphate (HBTU, 1 mmol), and diisopropylethylamine (1 mmol), and stirring for 2 hr at room temperature. After reaction is completed, the reactant was washed with dimethylformamide, dichloromethane, and dimethylformamide in order, which gave target compound without requiring separate purification.

Step 2: Preparation of PKCK-Fol-OH

P(Boc)-K(Boc)-C(Trt)-K-Wang resin-Fol of step 1 was dissolved in a mixed solution (20 ml) of TFA:TIS:EDT:thioanisole (Thioanisole):water=90:2.5:2.5:2.5:2.5, and stirred at room temperature for 2 hr. The mixture was purified with high performance liquid chromatography (HPLC, SHIMASU prominence HPLC). Shiseido capcell-pack 18C column was used for the HPLC, with mobile phase of water (A) containing 0.1% trifluoroacetic acid (TFA) and 0.1% TFA in acetonitrile(B). The gradient profile included passing of solvent A between 100% and 90% for 2 min, between 90% and 60% for 10 min, between 60% and 30% for 2 min, 30% for 3 min and between 30% and 100% for 3 min at a flow rate of 1 ml/min.

The resultant mixed solution was treated with excess 5° C. diethyl ether for precipitation. The resultant precipitates were centrifuged and removed of trifluoroacetic acid. After two more rounds, the solidified PKCK-Fol-OH was obtained.

Mass (m/z):measured: 898 (calculated: 898.02).

EXAMPLE 2

Preparation of PKCK-Fol-OH 2

Step 1: Preparation of P(Boc)-K(Boc)-C(Trt)-K-E(Trt)-Wang Resin-pteroic Acid

Pteroic acid derivative (0.15 mmol) of Preparative Example 2 or pteroic acid (0.15 mmol) was dissolved in dimethylsulfoxide (20 ml), and added with P(Boc)-K(Boc)-C(Trt)-K-E(Trt)-Wang resin (0.05 mmol) of Preparative Example 4, hydroxybenzotriazol (HOBt, 0.15 mmol), O-benzotriazol-N,N,N',N'-tetramethyl-uronium-hexafluoro-phosphate (HBTU, 0.15 mmol), and diisopropylethylamine (0.15 mmol), and stirred at room temperature for 3 hr. After reaction is concluded, the resin was washed with dimethylformamide, dichloromethane, and dimethylformamide in order, which gave target compound without requiring separate purification.

Step 2: Preparation of PKCK-Fol-OH

P(Boc)-K(Boc)-C(Trt)-K-E(Trt)-Wang resin-pteroic acid of Step 1 was dissolved in the mixture solution (20 ml) of TFA:TIS:EDT:thioanisole (Thioanisole):water=90:2.5:2.5:2.5:2.5, and stirred at room temperature for 2 hr. The mixture was purified with HPLC (SHIMASU prominence HPLC). Shiseido capcell-pack 18C column was used for the HPLC, with mobile phase of water (A) containing 0.1% trifluoroacetic acid (TFA) and 0.1% TFA in acetonitrile (B). The gradient profile included passing of solvent A between 100% and 90% for 2 min, between 90% and 60% for 10 min, between 60% and 30% for 2 min, 30% for 3min and between 30% and 100% for 3 min at a flow rate of 1 ml/min.

The resultant mixed solution was treated with excess 5° C. diethyl ether for precipitation. The resultant precipitates were centrifuged and removed of trifluoroacetic acid. After two more rounds, the solidified PKCK-Fol-OH was obtained.

Mass (m/z): measured: 898 (calculated: 898.02).

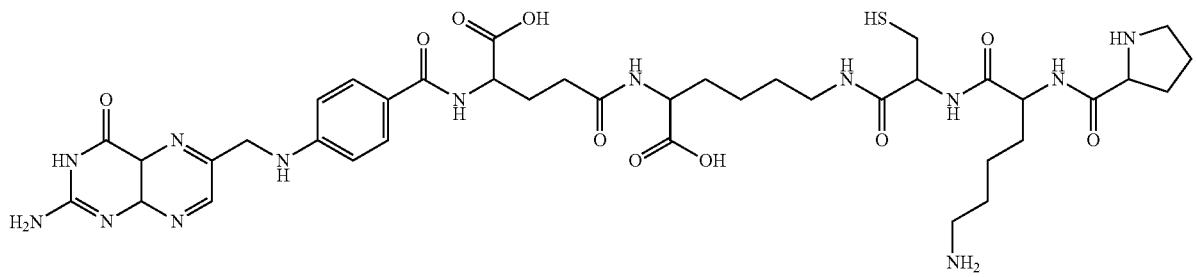 [SMILES: NCCCCC(NC(=O)C1CCCN1)C(=O)NC(CS)C(=O)NCCCCC(NC(=O)CCC(NC(=O)c1ccc(NCC2=NC3C(=O)NC(N)=NC3N=C2)cc1)C(=O)O)C(=O)O]

EXAMPLE 3

Preparation of PKCK-Fol-NH$_2$

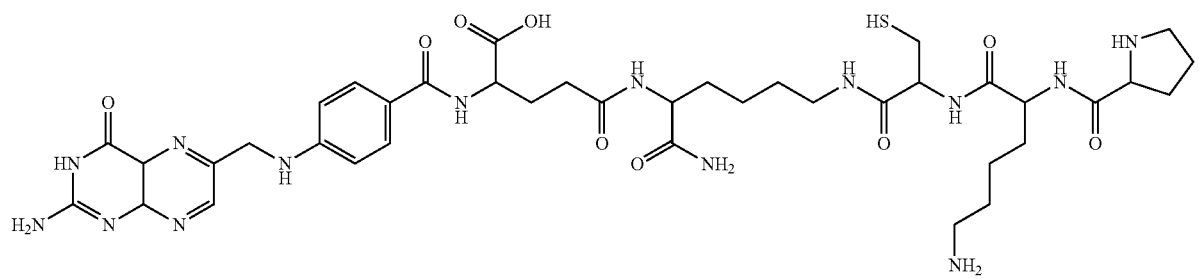

Target compound was obtained by the same method as that of Preparative Example 1, except for the difference of using P(Boc)-K(Boc)-C(Trt)-K-MBHA resin of Preparative Example 9 instead of P(Boc)-K(Boc)-C(Trt)-K-Wang resin of Preparative Example 3.

Mass (m/z): Measured: 911 (Calculated: 911.06).

EXAMPLE 4

Preparation of PKCK-E-Fol-OH

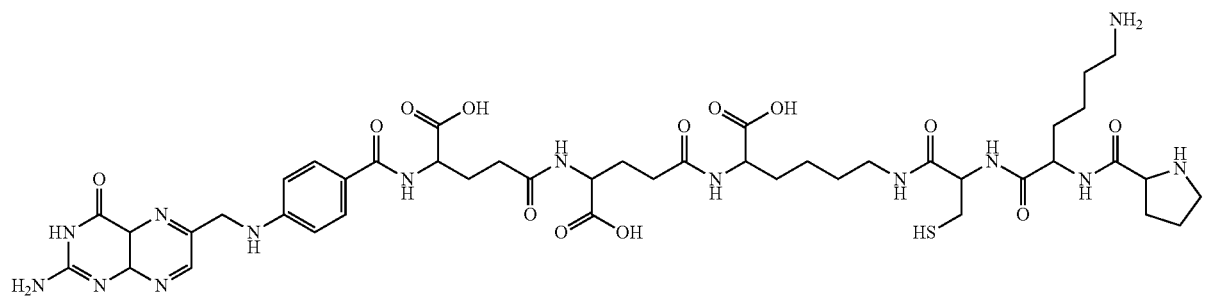 [SMILES: NCCCCC(NC(=O)C1CCCN1)C(=O)NC(CS)C(=O)NCCCCC(NC(=O)CCC(NC(=O)CCC(NC(=O)c1ccc(NCC2=NC3C(=O)NC(N)=NC3N=C2)cc1)C(=O)O)C(=O)O)C(=O)O]

Target compound was obtained by the same method as that of Preparative Example 2, except for the difference of using P(Boc)-K(Boc)-C(Trt)-K-E(Trt)-Wang resin of Preparative Example 4 instead of P(Boc)-K(Boc)-C(Trt)-K-Wang resin of Preparative Example 3

Mass (m/z): Measured: 1025 (Calculated: 1027.13).

EXAMPLE 5

Preparation of PK(FITC)CK-E-Fol-OH

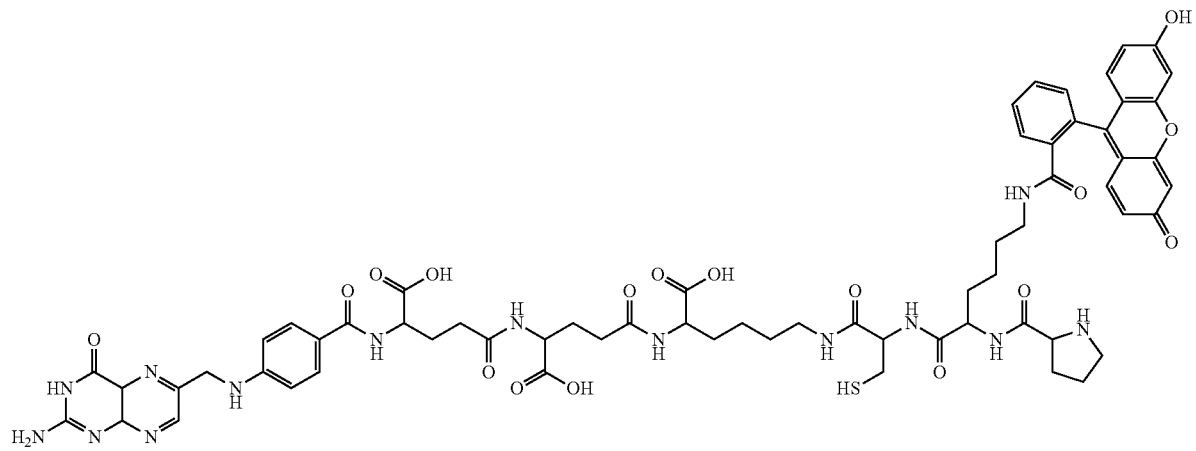 [SMILES: NC1=NC2N=CC(CNc3ccc(C(=O)NC(CCC(=O)NC(CCC(=O)NC(CCCCNC(=O)C(CS)NC(=O)C(CCCCNC(=O)c4ccccc4-c4c5ccc(=O)cc-5oc5cc(O)ccc45)NC(=O)C4CCCN4)C(=O)O)C(=O)O)C(=O)O)cc3)=NC2C(=O)N1]

Target compound was obtained by the same method as that of Preparative Example 1, except for the difference of using P(Boc)-(FITC)K(Boc)-C(Trt)-K-E(Trt)-Wang resin of Preparative Example 6 instead of P(Boc)-K(Boc)-C(Trt)-K-Wang resin of Preparative Example 3.

Mass (m/z): Measured: 1415 (Calculated: 1416.51).

EXAMPLE 6

Preparation of PSCK-(Beta-A)-Fol-OH

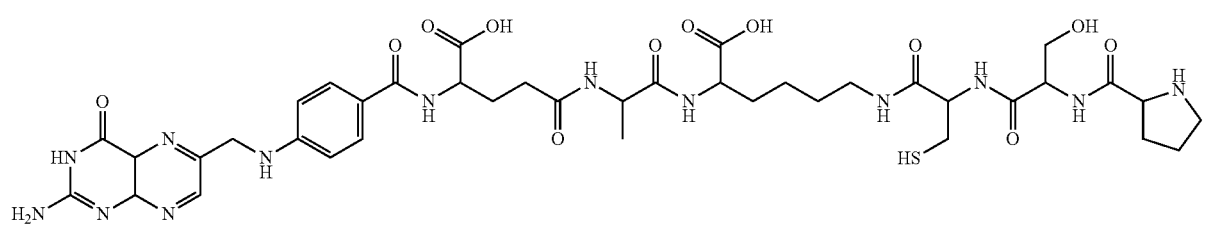 [SMILES: CC(NC(=O)CCC(NC(=O)c1ccc(NCC2=NC3C(=O)NC(N)=NC3N=C2)cc1)C(=O)O)C(=O)NC(CCCCNC(=O)C(CS)NC(=O)C(CO)NC(=O)C1CCCN1)C(=O)O]

Target compound was obtained by the same method as that of Preparative Example 2, except for the difference of using P(Boc)-S(t-Bu)-C(Trt)-K-(Beta-A)-E(Trt)-Wang resin of Preparative Example 7 instead of P(Boc)-K(Boc)-C(Trt)-K-E(Trt)-Wang resin of Preparative Example 4.

Mass (m/z): Measured: 927 (Calculated: 927).

EXAMPLE 7

Preparation of PDCK-(miniPEG)-Fol-NH2

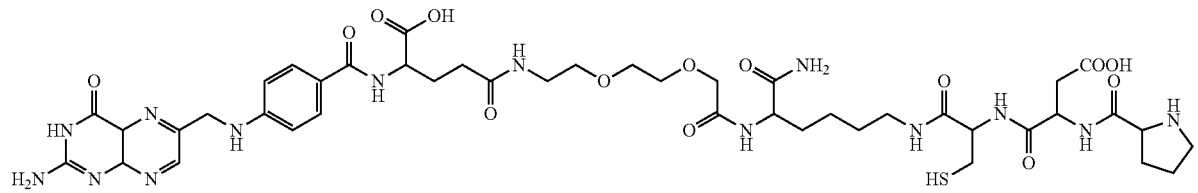 [SMILES: NC(=O)C(CCCCNC(=O)C(CS)NC(=O)C(CC(=O)O)NC(=O)C1CCCN1)NC(=O)COCCOCCNC(=O)CCC(NC(=O)c1ccc(NCC2=NC3C(=O)NC(N)=NC3N=C2)cc1)C(=O)O]

Target compound was obtained by the same method as that of Preparative Example 2, except for the difference of using P(Boc)-D(t-Bu)-C(Trt)-K-(miniPEG)-E(Trt)-MBHA resin of Preparative Example 8 instead of P(Boc)-K(Boc)-C(Trt)-K-E(Trt)-Wang resin of Preparative Example 4.

Mass (m/z): Measured: 1043 (Calculated: 1042).

EXAMPLE 8

Preparation of GKCK-Fol-OH

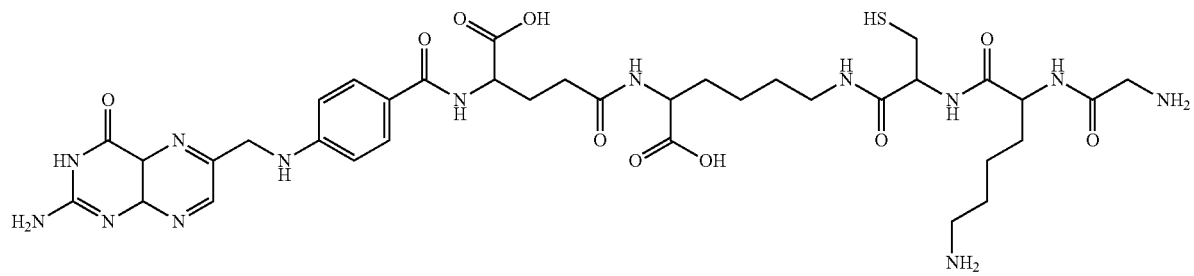 [SMILES: NCCCCC(NC(=O)CN)C(=O)NC(CS)C(=O)NCCCCC(NC(=O)CCC(NC(=O)c1ccc(NCC2=NC3C(=O)NC(N)=NC3N=C2)cc1)C(=O)O)C(=O)O]

Target compound was obtained by the same method as that of Preparative Example 2, except for the difference of using Gly(Boc)-K(Boc)-C(Trt)-K-E(Trt)-Wang resin instead of P(Boc)-K(Boc)-C(Trt)-K-E(Trt)-Wang resin of Preparative Example 4.

Mass (m/z): Measured: 857 (Calculated: 857.95).

EXAMPLE 9

Preparation of GKC-Dea-Fol-OH

Target compound was obtained by the same method as that of Preparative Example 2, except for the difference of using G(Alloc)-K(Boc)-C(Trt)-Dea(Fmoc)-Wang resin instead of P(Boc)-K(Boc)-C(Trt)-K-E(Trt)-Wang resin of Preparative Example 4 (wherein, Dea is Etheylenediamine).

Mass (m/z): Measured: 857 (Calculated: 857.95).

EXAMPLE 10

Radiolabeling PKCK-Fol-OH with $^{99m}Tc$

The compound of Example 1 was radiolabeled with $^{99m}Tc$ The glucopeptonate (GH) kit containing 20 mg GH and 0.45 mg stannous chloride ($SnCl_2$) was dissolved with 400 µl sodium $^{99m}Tc$ pertechnetate ($Na^{99m}TcO_4$) from generator containing up to 370 MBq, and was allowed to stand for 10 min at room temperature for preparing $^{99m}Tc$-CH. The reaction solution was analyzed by ITLC on silica gel strips with saline or MEK as the mobile phase to check the amount of colloid formation. In the saline as a mobile phase, free $^{99m}TcO_4^-$ and $^{99m}Tc$-CH migrate at Rf 1.0, and colloid remains at Rf 0.0. In the MEK, free $^{99m}TcO_4^-$ migrates at Rf 1.0, and $^{99m}Tc$-GH and colloid remain at Rf 0.0, respectively. PKCK-fol-OH ligand, the compound prepared at Example 1, was dissolved in distilled water so give a concentration of $10^{-3}$ M ($10^{-6}$ mol/ml). A 100 µl aliquot of $^{99m}Tc$-GH from this vial (370 MBq, 10 mCi) was then added to various concentrations of the PKCK-fol ligand ($10^{-7}$ mol, $10^{-8}$ mol 10$^{-9}$ mol) in 400 µl of 50 mM sodium acetate buffer (pH 5.5) and the reaction was allowed to stand for 20 mini at room temperature. The radiochemical purity (RCP) and the efficiency of radiolabeling yield of the compounds were determined by RP-HPLC on Waters HPLC system equipped with Waters 2695 pump, UV detector (Waters 2487), RI detector (In/US γ-detector system), and a X-terra C-18 column (5 µm, 4.6×250 mm) at a flow rate of 1.0 ml/min with a gradient mobile phase. The mobile phase consisted of 0.1% trifluoroacetic acid (TFA) in water (A) and 0.1% TFA in acetonitrile (B). The elution profile was like that, solvent (A) 100% to 90% for 2 min, 90% to 60% for 10 min, 60% to 30% for 2 min, 30% for 3 mm and 30% to 100% for 3 min. The complex purified with RP-HPLC was thus obtained, and the radiochemical purity thereof was measured as provided in FIGS. 2 and 3.

Figure 2:
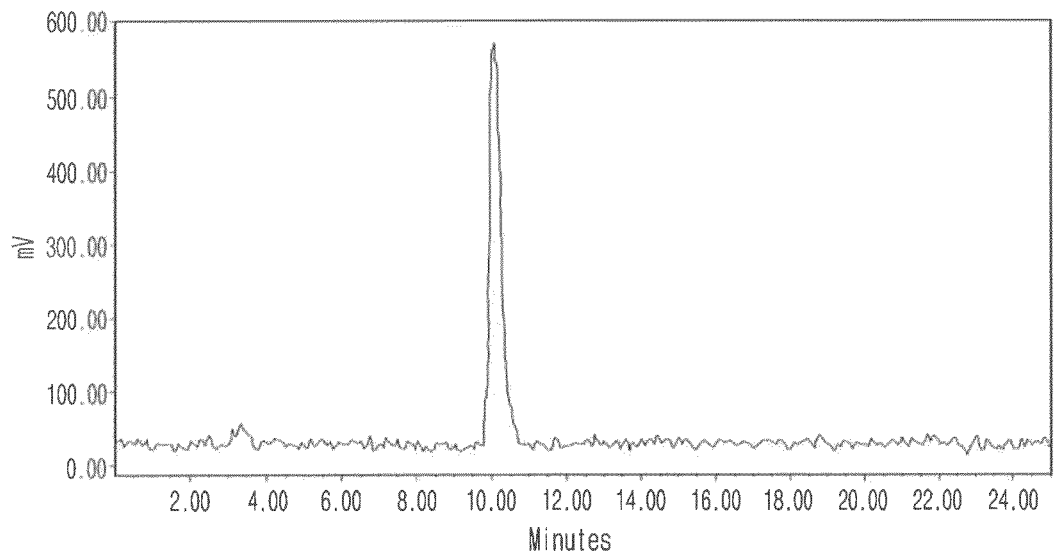
FIG. 2 shows HPLC of $^{99m}$Tc-labeled PKCK-fol-OH prepared in Example 10, according to the present invention.
Figure 3:
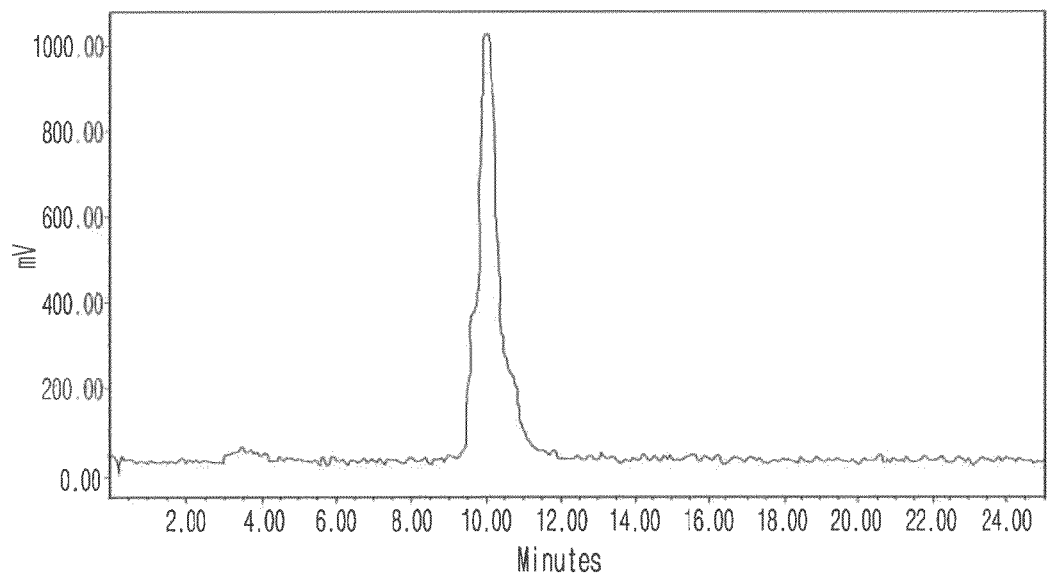
FIG. 3 shows HPLC analysis performed after incubation of $^{99m}$Tc-labeled PKCK-fol-OH, prepared in Example 10 in serum for 24 hr, according to the present invention.

Referring to FIGS. 2 and 3, the radioisotope-labeled, novel $N_3S_1$ chelator-folate had radiochemical purity (RCP) exceeding 98%, with labeling yield measured as 37 GBq/umol, and retention time measured as 10.1 min. Further, the radiolabeled compound showed excellent in vitro stability in saline and serum at 37° C. for 24 hr, thus indicating stability as high as 96% or above.

EXAMPLE 11

Radiolabeling PKCK-E-Fol-OH with $^{99m}Tc$

Complex compound was obtained with the same method of Example 10, except for the difference of radiolabeling $^{99m}TC$ on PKDK-E-Fol-OH prepared at Example 4, instead of radiolabeling $^{99m}TC$ on PKCK-Fol-OH prepared at Example 1. The radiochemical purity of the complex compound was 98% or above, with retention time measured as 10.4 min.

EXAMPLE 12

Radiolabeling GKC-Dea-Fol-OH with $^{99m}Tc$

Complex compound was obtained with the same method of Example 10, except for the difference of radiolabeling $^{99m}TC$ on GKC-Dea-Fol-OH prepared at Example 9, instead of radiolabeling $^{99m}TC$ on PKCK-Fol-OH prepared at Example 1. The radiochemical purity of the complex compound was 98% or above, with retention time measured as 10.0 min.

EXPERIMENTAL EXAMPLE 1

Cell Uptake and Folate-receptor (FR) Binding Affinity

The following experiment was conducted to evaluate cell uptake and folate-receptor binding affinity of the radiolabeled folate complex according to the present invention.

FR-positive KB tumor cells (human oral epidermoid carcinoma) which overexpress FR were grown in T-flask until 80%-90% confluence at 37° C. and 5% $CO_2$ with folid-acid free (deficient) RPMI 1640 medium (FFRPMI) containing 10% heat-inactivated fetal bovine serum (FBS). About $8\times10^5$ cells were seeded in 12 well-plates for 24 hr for the in vitro cell uptake and binding affinity studies. Cells were rinsed twice with ice-cold PBS and pre-incubated with 850 μl of fresh FFRPMI without FBS at 37° C. for 30 min. The solution of the $^{99m}Tc$-labeled folate complex (18.5 kBq) prepared using PKCK-fol-OH compound of Example 1 was added and the well plates were incubated at 37° C. for 10, 30, 60, 120 and 180 min for time-dependent cell uptake assay. Blocking experiments were also carried out with cells which were pre-incubated with excess cold folic acid (100 μM) for 30 mm before addition of radiolabeled compound. After incubation, the well plates were washed twice with ice-cold PBS.

After that, the cells were washed with an acid wash buffer (50 mM glysine-HCL buffer, pH 2.4), to remove membrane bound radioligand, and the supernatant was collected to measure the membrane bound fraction of radioactivity. Cells were lysed with 1N NaOH, transferred and measured the internalised fraction of radioactivity with γ-counter. Counted radioactivity in membrane bound fraction and internalized fraction could be ascribed to the sum of cell uptake. The cell uptake data was expressed as % cell uptake (cell uptake/total added activity). Each data represents a result of the sewerage of triplicate wells. The affinity of PKCK-fol was determined using competitive binding assay. $^{99m}Tc$-PKC-fol was used as radioligand in this assay. Cells were harvested with typsin and washed with PBS buffer, and $8\times10^5$ cells were seeded in 12-well plates. After incubation with $^{99m}Tc$-labeled folate (PKCK-fol-OH, 37 kBq) and appropriate dilutions of nonlabeled folate and PKC-fol-OH in 1 ml of the FFRPMI at 37° C. for 1 hr, incubation was interrupted by removal of the supernatant and rapid washing three times with FFRPMI. After that, the cells were collected to measure the radioactivity with γ-counter. $IC_{50}$ values of the folate and pKCK-fol-OH were calculated by non-linear regression using GraphPad Prism software, which indicated 20 nM and 160 nM. Each point represents a result of the average of triplicate (see FIG. 4).

Figure 4:
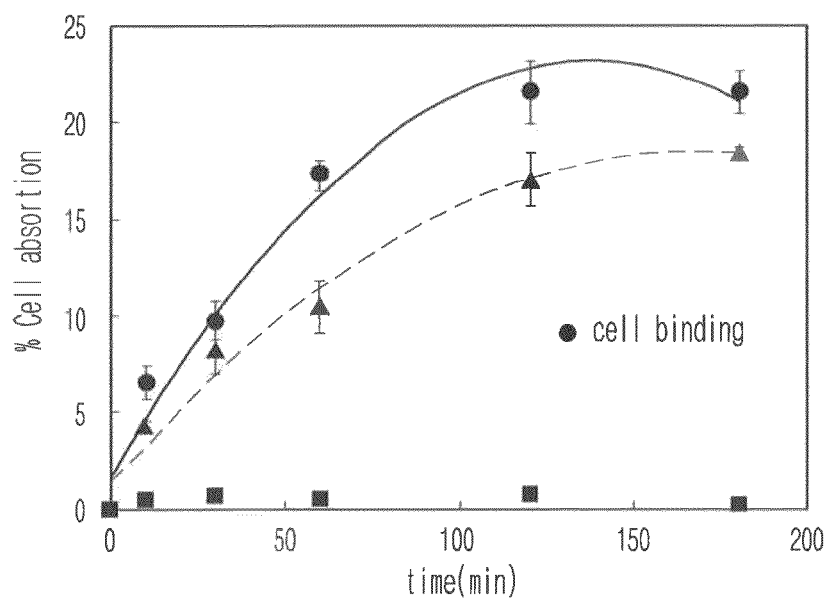
FIG. 4 shows cell binding and internalization of $^{99m}$Tc-labeled PKCK-fol-OH in FR-positive KB cells according to Experimental Example 1.
Figure 5:
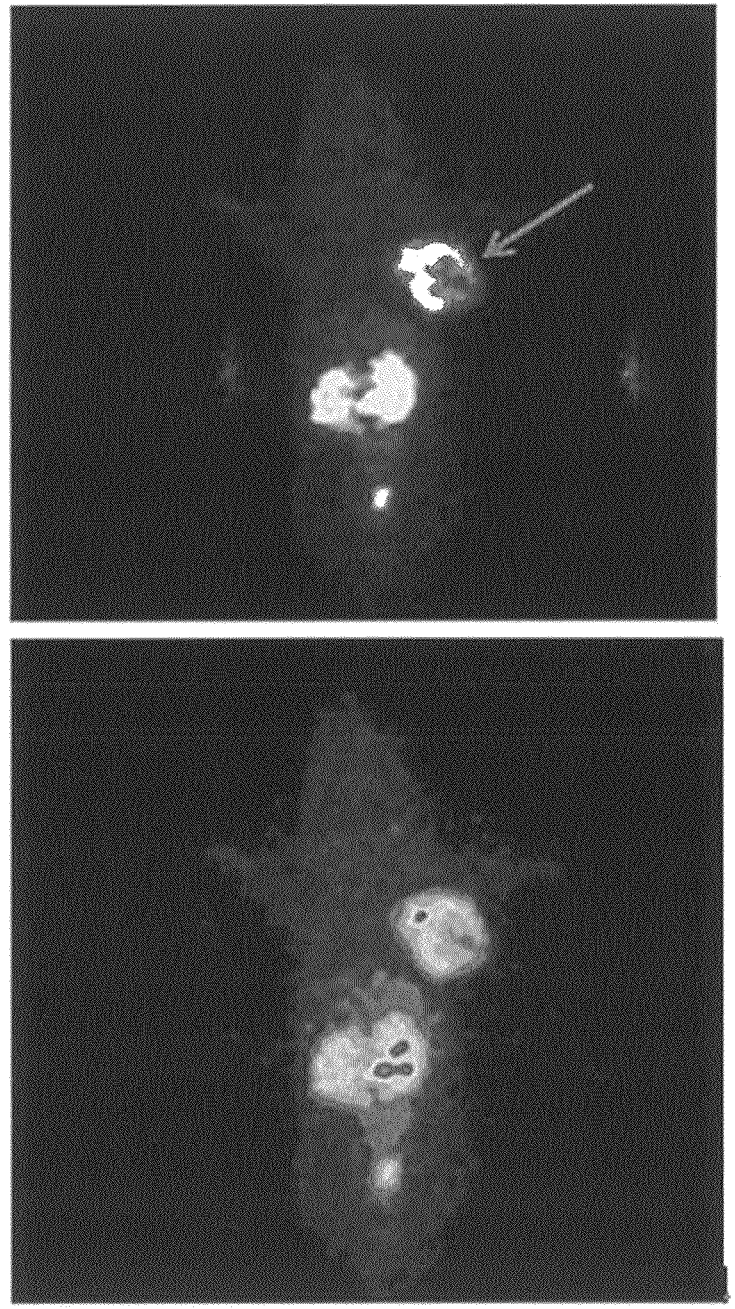
FIG. 5 shows representative SPECT images of nude mice bearing the KB tumor at 3 hr after injection of $^{99m}$Tc-labeled PKCK-fol-OH (185 Mbq, 5 mCi) according to Experimental Example 3.
Figure 6:
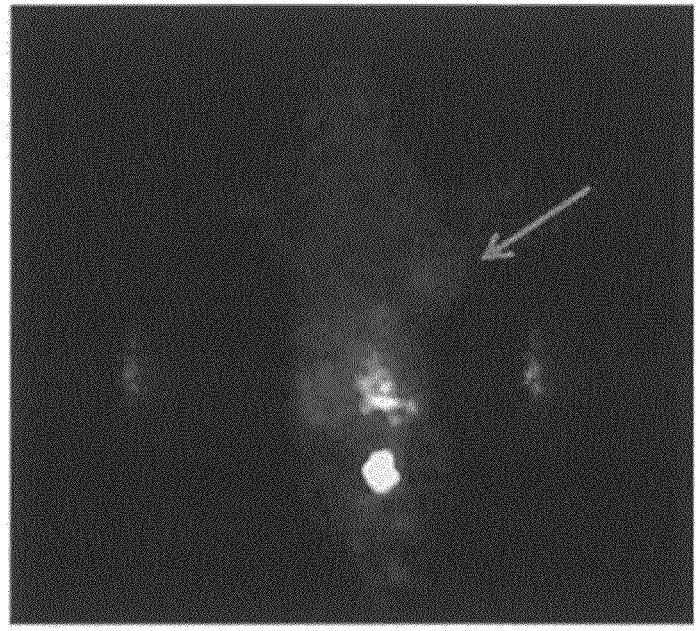
FIG. 6 shows representative SPECT images of nude mice bearing the KB tumor after injection of $^{99m}$Tc-labeled PKCK-fol-OH (185 Mbq, 5 mCi) with excess folate (0.25 μmol) according to Experimental Example 3.
Figure 6:
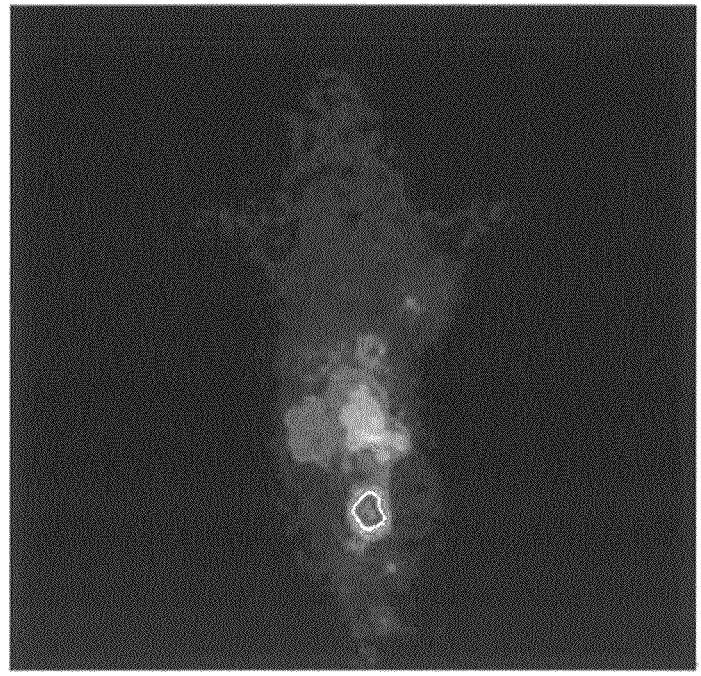
Figure 7:
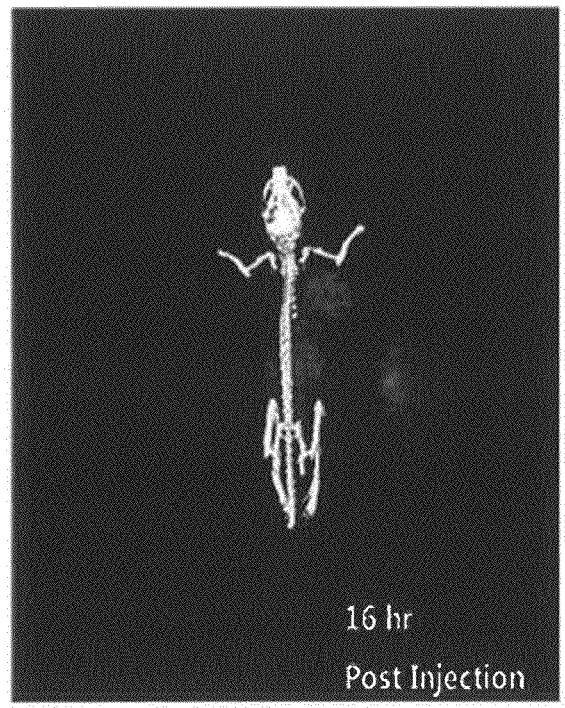
FIG. 7 shows representative 3D reconstruction SPECT/CT at 18 hr after injection of $^{99m}$Tc-labeled PKCK-fol-OH in the tumor and kidney, respectively, according to Experimental Example 3.
Figure 8:
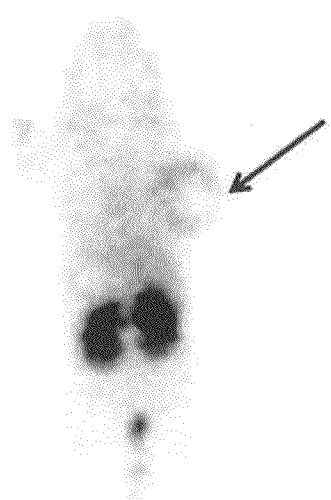
FIG. 8 shows representative image at 1 hr after injection of $^{99m}$Tc-PKCK-fol-OH in KB xenograft according to Experimental Example 3.
Figure 9:
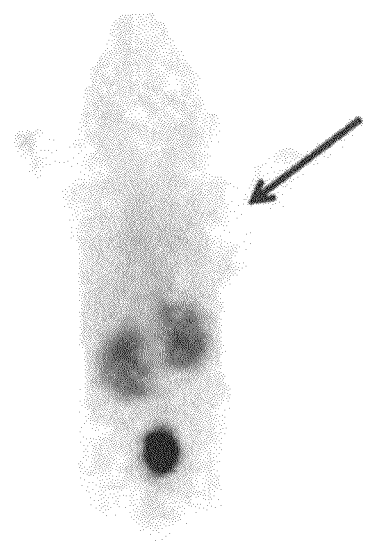
FIG. 9 shows representative image at 1 hr after blocking of folate and injection of $^{99m}$Tc-PKCK-fol-OH according to Experimental Example 3.
Figure 10:
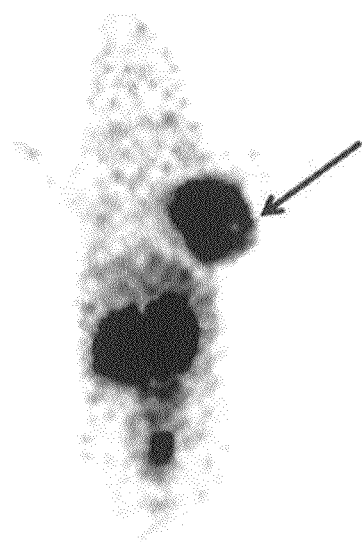
FIG. 10 shows representative image at 3 hr after injection of $^{99m}$Tc-PKCK-fol-OH in KB xenograft according to Experimental Example 3.
Figure 11:
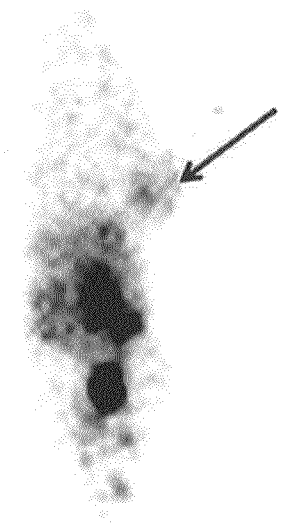
FIG. 11 shows representative image at 3 hr after blocking of folate and injection of $^{99m}$Tc-PKCK-fol-OH according to Experimental Example 3.
Figure 12:
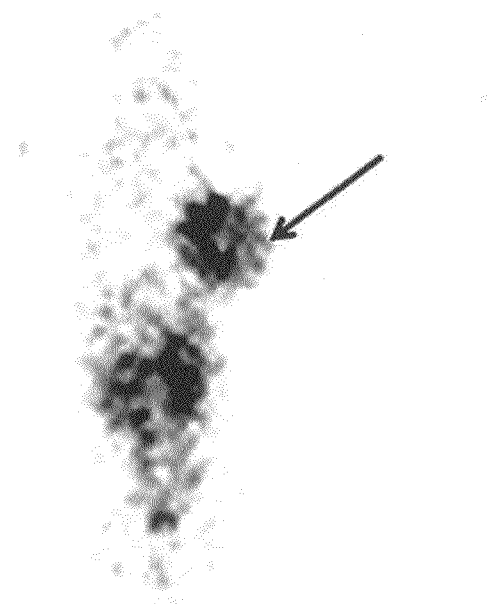
FIG. 12 shows representative image at 18 hr after injection of $^{99m}$Tc-PKCK-fol-OH in KB xenograft according to Experimental Example 3.
Figure 13:
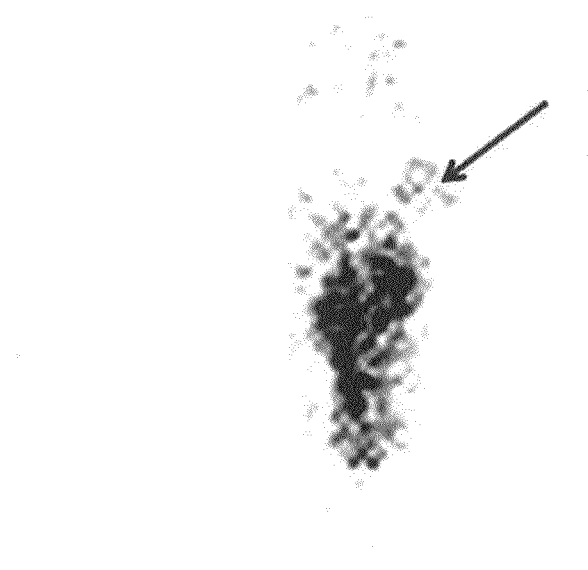
FIG. 13 shows representative image at 18 hr after blocking of folate and injection of $^{99m}$Tc-PKCK-fol-OH according to Experimental Example 3.

Referring to FIG. 4, the radioactive folate exhibited cell affinity and internalization rate which increased time dependently.

Accordingly, since the novel $N_3S_1$ chelator-folate derivative according to the present invention forms stable complex with radioisotope, and also shows superior cell affinity and internalization rate of the complex, it can be advantageously used as a composition for diagnosing or treating cancer.

EXPERIMENTAL EXAMPLE 2

Biodistribution Study for $^{99m}Tc$-PKCK-fol-OH in KB Xenografts Model

The following experiment was carried out to evaluate tumor and body organ uptakes of $^{99m}Tc$-labeled PKCK-fol-OH.

The stock solution of the $^{99m}Tc$-labeled PKCK-fol-OH used in the animal studies was prepared for $10^{-8}$ mol/ml with an activity of 370 MBq. Solutions for injection were prepared by the dilution of the stock solution to obtain a desired volumetric activity of 3.7 MBq/ml. The biodistribution experiments for the $^{99m}Tc$-labeled PKCK-fol-OH were performed with KB-bearing female nude mice (provided by OrientBio, Republic of Korea). The mice were maintained a folate-deficient rodent chow (Harlan laboratories, Inc., USA) for two weeks to minimize the level of folate concentration. After tumor was allowed to grow for 2-3 weeks, the mice were administered 370 kBq (10 uCi)/100 μl intravenously. At 30 min, 1 hr, 3 hr and 24 hr, the animals were sacrificed.

Table 1 below lists biodistribution results measured at 30 min, 1 hr, 3 hr and 24 hr after injection.

TABLE 1

| | $^{99m}$To-PKCK-gamma Glu-folate | | | |
| Organ | 30 min | 1 hr | 3 hr | 24 hr |
| --- | --- | --- | --- | --- |
| Blood | 0.64 ± 0.26 | 0.36 ± 0.06 | 0.18 ± 0.05 | 0.06 ± 0.02 |
| Liver | 7.21 ± 1.58 | 5.42 ± 1.85 | 2.83 ± 0.60 | 1.09 ± 0.07 |
| Kidney | 76.47 ± 5.04 | 77.19 ± 5.43 | 41.48 ± 12.08 | 7.49 ± 1.90 |
| Spleen | 0.47 ± 0.13 | 0.36 ± 0.03 | 0.30 ± 0.07 | 0.10 ± 0.03 |
| Heart | 2.25 ± 0.47 | 1.73 ± 0.27 | 1.03 ± 0.32 | 0.10 ± 0.06 |
| Sm Int | 0.93 ± 0.54 | 0.43 ± 0.05 | 0.27 ± 0.12 | 0.10 ± 0.05 |
| Lg Int | 2.43 ± 1.38 | 3.43 ± 0.73 | 1.48 ± 0.64 | 1.38 ± 0.86 |
| Lung | 1.70 ± 0.35 | 1.45 ± 0.33 | 0.63 ± 0.26 | 0.12 ± 0.06 |
| Stomach | 1.92 ± 0.26 | 1.20 ± 0.05 | 0.55 ± 0.16 | 0.13 ± 0.04 |
| Tumor | 2.60 ± 0.53 | 2.96 ± 0.51 | 2.24 ± 0.27 | 0.91 ± 0.28 |
| Tumor/blood | 4.38 ± 0.92 | 8.35 ± 1.12 | 13.17 ± 2.78 | 15.15 ± 4.36 |
| Tumor/kidney | 0.03 ± 0.01 | 0.04 ± 0.01 | 0.06 ± 0.01 | 0.12 ± 0.02 |
| Tumor/liver | 0.38 ± 0.14 | 0.58 ± 0.17 | 0.82 ± 0.20 | 0.83 ± 0.24 |

Referring to Table 1, radioisotope-labeled PKCK-fol-OH had the high tumor uptake of 2.60±0.53% ID/g at 30 min p.i. and 2.24±0.27% ID/g at 3 hr p.i. with very fast blood clearance (0.64±0.26% ID/g and 0.18±0.05% ID/g at at 30 min and 3 hr p.i., respectively). As a result, the tumor/blood ratios increased from 4.35±0.92 at 30 min to 13.17±2.78% ID/g at 3 hr p.i. Meanwhile, high radioactivity in the kidney was found in the nude mice bearing KB tumor xenograft (77.19±5.43% ID/g and 41.48±12.08% ID/g at 1 hr and 3 hr p.i., respectively). Its liver uptake was 5.42±1.85% ID/g and 2.83±0.60% ID/g at 1 hr and 3 hr p.i., respectively. In other organs, such as lung, heart, stomach and intestines, the uptake of the radiolabeled compound kept at a low level.

Accordingly, the novel $N_3S_1$ chelator-folate derivative according to the present invention is labeled with radioisotope to provide stable complex, so that the complex with low uptake in various organs including blood, lung, heart and stomach, but with high uptake in tumor, can be advantageously used as a composition for diagnosis or treatment of tumor.

EXPERIMENTAL EXAMPLE 3

In vivo SPECT Imaging

The following experiment was conducted to evaluate SPECT imaging effect for the diagnosis purpose of the radioisotope-labeled, novel $N_3S_1$ chelator-folate.

For in vivo SPECT imaging, the mice were maintained a folate-deficient rodent chow for two weeks, and were administered with 185 MBq (5 mCi)/100 μl. Blocking studies have been performed by coadministration of folic acid (100 μg/100 μl) 5 min prior to the injection of radiofolate. Planar gamma camera images were acquired and reconstructed at 5 min, 1 hr and 4 hr. SPECT and CT data for 3D reconstruction were acquired with the software after 18 hr, and the result is shown in FIGS. 5 to 13.

Referring to FIGS. 5 to 13, the radioisotope-labeled, novel $N_3S_1$ chelator-folate according to the present invention was stably SPECT imaged in vivo.

Accordingly, since the radioisotope-labeled, novel $N_3S_1$ chelator-folate according to the present invention has stable uptake in vivo and provides excellent imaging effect on medical imaging equipment such as SPECT, the radioisotope-labeled, novel $N_3S_1$ chelator-folate according to the present invention, can be advantageously used as a composition for diagnosis or treatment of tumor.

The foregoing exemplary embodiments and advantages are merely exemplary and are not to be construed as limiting the present invention. The present teaching can be readily applied to other types of apparatuses. Also, the description of the exemplary embodiments of the present inventive concept is intended to be illustrative, and not to limit the scope of the claims.

What is claimed is:

1. A $N_3S_1$ chelator-folate derivative expressed by Chemical Formula 1 below, or a pharmaceutically acceptable salt thereof:

[Chemical formula 1]

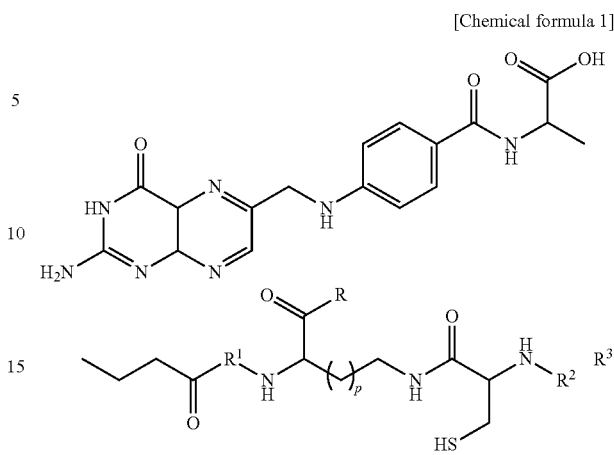

wherein, R is hydroxy or amine;
$R^1$ is nonbonding,

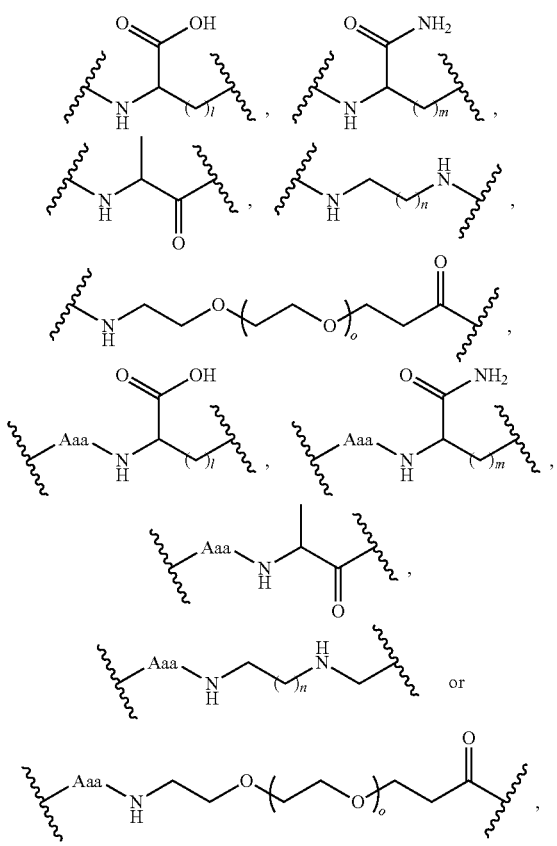

wherein Aaa is any one selected from 1 to 3 amino acids, and derivatives thereof;
l is an integer between 1 and 10;
m is an integer between 1 and 10;
n is an integer between 1 and 10;
o is an integer between 1 and 20;
$R^2$ is amino acid selected from a group consisting of alanine, arginin, asparagine, aspartic acid, cystine, glutaric acid, glutamine, glycine, histidine, iso-leucine, leucine, lysine, methionine, phenylalanine, proline, serine, threonine, tryptophan, tyrosine and valine;

$R^3$ is

[structures]

$R^4$ is halogen, hydroxy or amine;
$R^5$ is alkyl between $C_1$ and $C_4$; and
P is an integer between 1 and 4.

2. The $N_3S_1$ chelator-folate derivative or pharmaceutically acceptable salt thereof as set forth in claim 1, wherein R is hydroxy or amine;
$R^1$ is nonbonding,

[structures]

wherein

Aaa is any one selected from 1 to 3 amino acids, D-form amino acid, and derivative thereof;
l is an integer between 1 and 4;
m is an integer between 1 and 4;
n is an integer between 1 and 6; and
o is an integer between 1 and 10,
$R^2$ is amino acid selected from a group consisting of alanine, arginin, asparagine, aspartic acid, cystine, glutaric acid, glutamine, glycine, hisitidine, iso-leucine, leucine, lysine, methionine, phenylalanine, proline, serine, threonine, tryptophan, tyrosine and valine;
$R^3$ is

[structures]

$R^4$ is fluoro, hydroxy or amine;
$R^5$ is methyl or ethyl; and
P is an integer between 1 and 4.

3. A method for preparation of the $N_3S_1$ chelator-folate derivative of claim 1, comprising, as represented by Reaction Formula 1 below;

preparing folate derivative of Chemical Formula 4 by allowing the folic acid derivative of Chemical Formula 2 to react with a compound of Chemical Formula 3 (step 1); and preparing a compound of Chemical Formula 1 by removing resin, which is solid phase support of the folate derivative of Chemical Formula 4 prepared at step 1 under acidic condition (step 2):

[Reaction Formula 1]

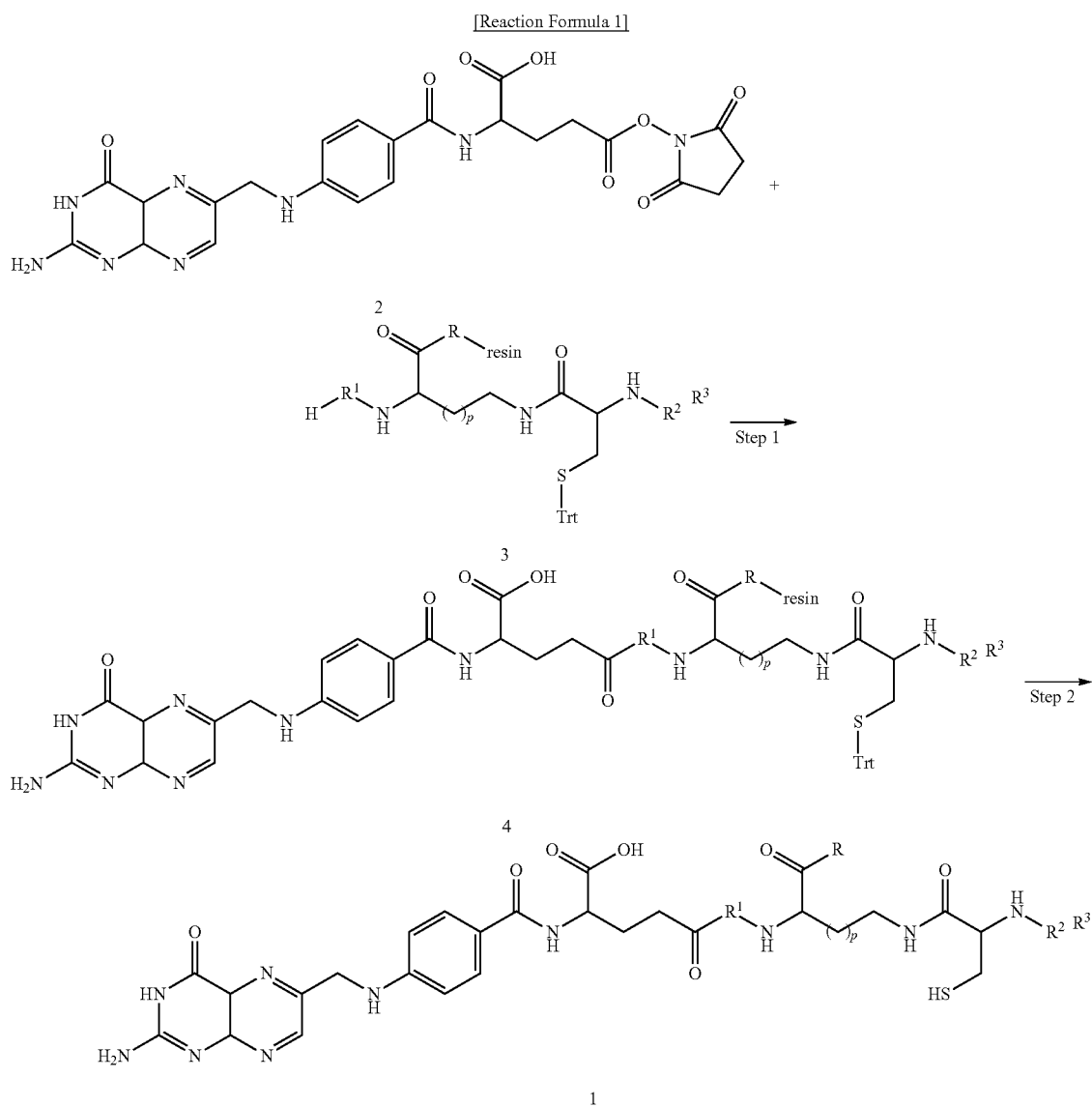

wherein,
resin is solid phase support; and
Trt is trityl group.

4. The method of claim 3, wherein the compound represented by Chemical Formula 3 of the Reaction Formula 1 is prepared by a method comprising, as represented by Reaction Formula 2 below;

preparing a compound represented by Chemical Formula 5 by allowing lysine protected with Alloc protecting group to react with cysteine protected with Fmoc protecting group (step 1);

preparing a compound represented by Chemical Formula 7 by allowing the compound of Chemical Formula 5 prepared at step 1 to react with a compound represented by Chemical Formula 6 (step 2);

preparing a compound represented by Chemical Formula 9 by allowing the compound of Chemical Formula 7 prepared at step 2 to react with a compound represented by Chemical Formula 8 (step 3); and preparing a compound represented by Chemical Formula 3, by allowing the compound of Chemical Formula 9 prepared at step 3 to react with a compound represented by Chemical Formula 10 (step 4):

[Reaction Formula 2]

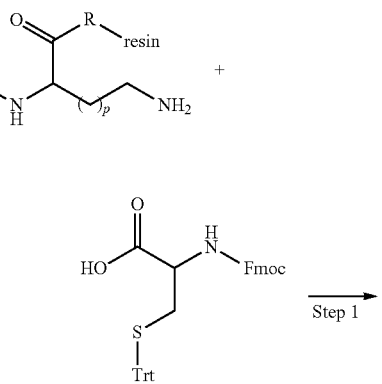

39

-continued

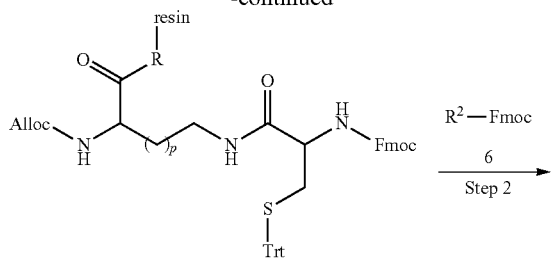

5

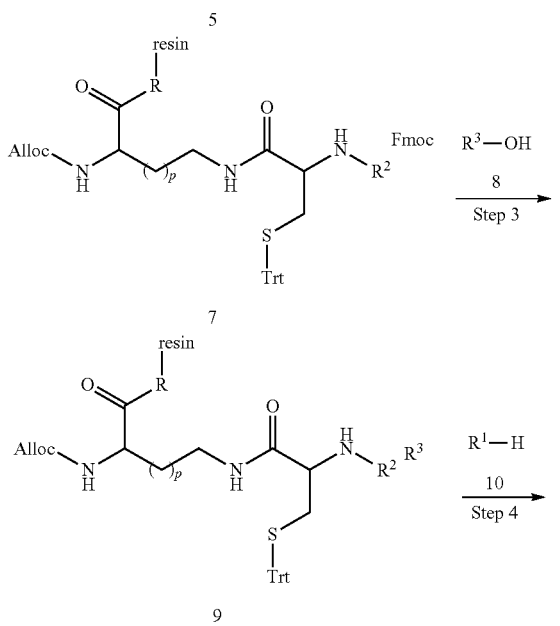

40

-continued

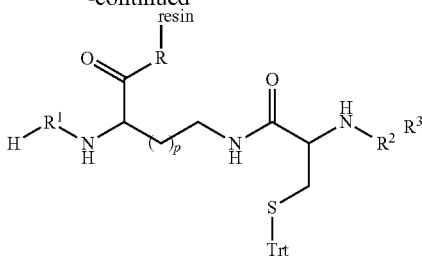

3 wherein,
resin is solid phase support;
Alloc is allylcarbamate;
Fmoc is fluorenylmethyloxycarbonyl group; and
Trt is trityl group.

5. A preparation method of the $N_3S_1$ chelator-folate derivative of claim 1, comprising, as represented by Reaction Formula 3 below:

preparing folate derivative of Chemical Formula 4 by allowing pteroic acid derivative of Chemical Formula 11 to react with a compound of Chemical Formula 12 (step 1); and preparing a compound of Chemical Formula 1 by removing resin, which is solid phase support of the folate derivative of Chemical Formula 4 prepared at step 1, under acidic condition (step 2):

[Reaction Formula 3]

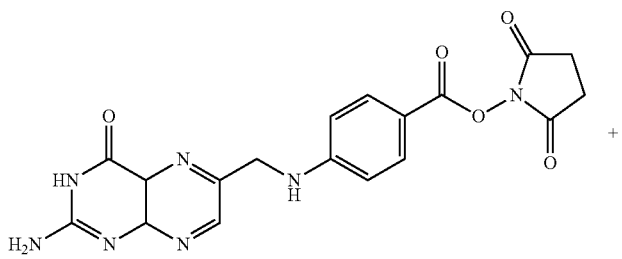

11

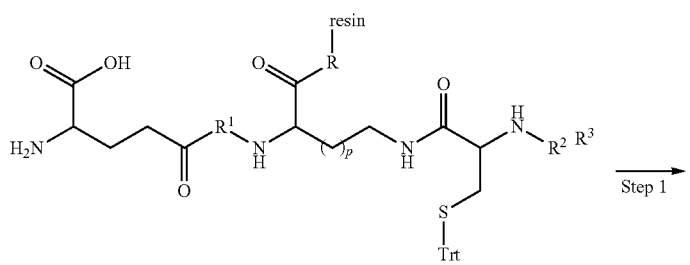

12

-continued

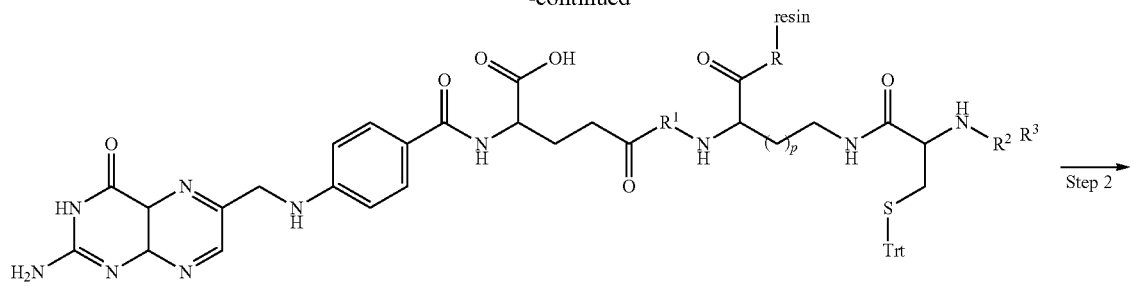

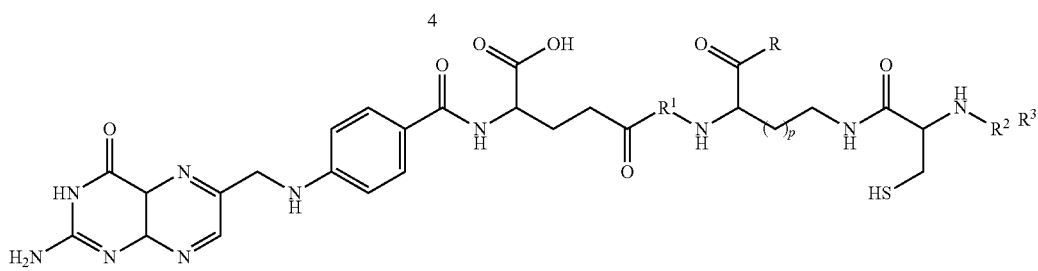

wherein,
resin is solid phase support; and
Trt is trityl group.

6. The method of claim 5, wherein the compound represented by Chemical Formula 12 of the Reaction Formula 3 is prepared by a method comprising, as represented by Reaction Formula 4 below:

preparing a compound represented by Chemical Formula 14, by allowing a compound represented by Chemical Formula 3 to be conjugated with glutamic acid represented by Chemical Formula 13 (step 1); and preparing a compound represented by Chemical Formula 12 by deprotecting the compound of Chemical Formula prepared at step 1 (step 2):

[Reaction Formula 4]

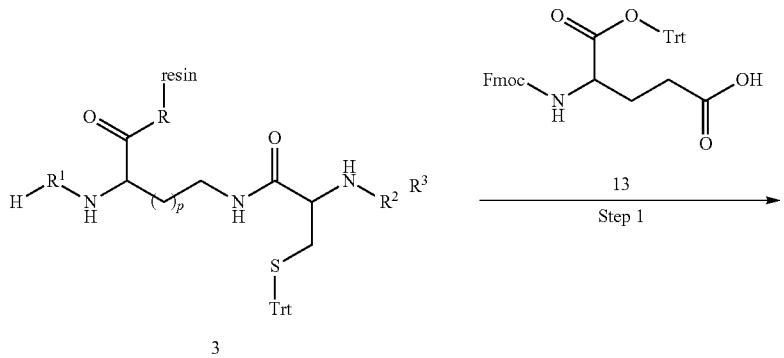

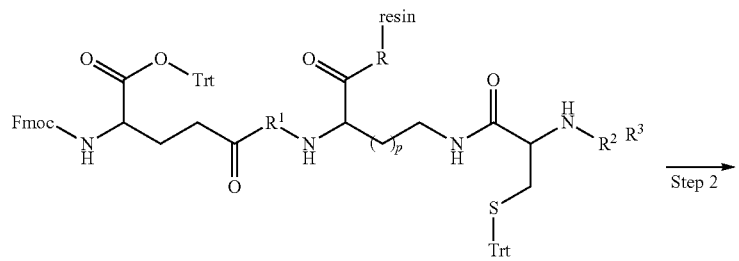

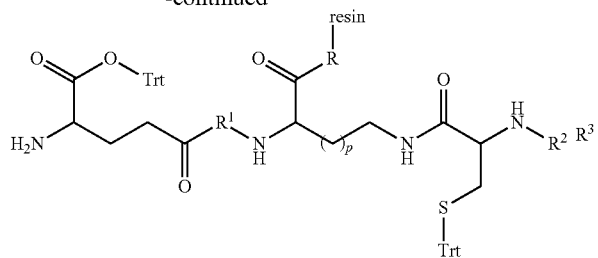

12 wherein, resin is solid phase support;

Fmoc is fluorenylmethyloxycarbonyl group; and

Trt is trityl group.

7. The method of claim 3, wherein the solid phase support is Wang resin or Merrifield resin.

8. The $N_3S_1$ chelator-folate derivative of claim 1, further labeled with radioisotope.

9. The radioisotope-labeled $N_3S_1$ chelator-folate derivative of claim 8, wherein the radioisotope is technetium or rhenium.

10. A method for preparation of a radioisotope-labeled complex, comprising transchelating the $N_3S_1$ chelator-folate derivative of claim 8, using ligand exchange reaction kit.

11. A composition for diagnosis of tumor, comprising the radioisotope-labeled $N_3S_1$ chelator-folate derivative of claim 8 as an active ingredient.

12. A composition for treatment of tumor, comprising the radioisotope-labeled $N_3S_1$ chelator-folate derivative of claim 8 as an active ingredient.

13. A kit for radioisotope-labeling the $N_3S_1$ chelator-folate derivative of claim 1.

* * * * *